(12) United States Patent
Matsumoto et al.

(10) Patent No.: US 11,045,081 B2
(45) Date of Patent: Jun. 29, 2021

(54) ENDOSCOPE SYSTEM

(71) Applicant: OLYMPUS CORPORATION, Tokyo (JP)

(72) Inventors: Koji Matsumoto, Tokyo (JP); Tetsuhiro Oka, Tokyo (JP); Sho Shinji, Tokyo (JP)

(73) Assignee: OLYMPUS CORPORATION, Tokyo (JP)

( * ) Notice: Subject to any disclaimer, the term of this patent is extended or adjusted under 35 U.S.C. 154(b) by 0 days.

(21) Appl. No.: 16/702,964

(22) Filed: Dec. 4, 2019

(65) Prior Publication Data

US 2020/0100660 A1  Apr. 2, 2020

Related U.S. Application Data

(63) Continuation of application No. PCT/JP2017/021667, filed on Jun. 12, 2017.

(51) Int. Cl.
*A61B 1/045* (2006.01)
*G06T 7/586* (2017.01)
(Continued)

(52) U.S. Cl.
CPC .......... *A61B 1/045* (2013.01); *A61B 1/00009* (2013.01); *A61B 1/06* (2013.01);
(Continued)

(58) Field of Classification Search
CPC ....... A61B 1/045; A61B 1/00009; A61B 1/06; A61B 1/0646; A61B 1/0684; A61B 1/05;
(Continued)

(56) References Cited

U.S. PATENT DOCUMENTS 6,464,633 B1   10/2002   Hosoda et al.
7,519,096 B2    4/2009   Bouma et al.
(Continued)

FOREIGN PATENT DOCUMENTS

EP   2229870 A1    9/2010
EP   2520214 A1   11/2012
(Continued)

OTHER PUBLICATIONS

Office Action dated Jun. 19, 2020 received in U.S. Appl. No. 16/691,865.
(Continued)

*Primary Examiner* — Jared Walker
(74) *Attorney, Agent, or Firm* — Scully, Scott, Murphy & Presser, P.C.

(57) ABSTRACT

An endoscope system according to the present invention includes: a second illumination unit that emits second illumination light; a first illumination unit that emits, simultaneously with the second illumination light, first illumination light that is light of a different wavelength band from the second illumination light and is for imaging two sets of image information about a subject different depths; an imaging unit that simultaneously images a first illumination image of the subject illuminated with the first illumination light and a second illumination image of the subject illuminated with the second illumination light; a separation processing unit that separates the two sets of image information from the first illumination image; and a separated-image creating unit that processes the second illumination image using the two sets of image information to create separated images.

8 Claims, 16 Drawing Sheets

(51) Int. Cl.
  *A61B 1/00* (2006.01)
  *A61B 1/06* (2006.01)
  *H04N 5/225* (2006.01)
(52) U.S. Cl.
  CPC .......... *A61B 1/0646* (2013.01); *A61B 1/0684* (2013.01); *G06T 7/586* (2017.01); *H04N 5/2256* (2013.01); *G06T 2207/10048* (2013.01); *G06T 2207/10068* (2013.01); *G06T 2207/10152* (2013.01); *G06T 2207/20224* (2013.01); *H04N 2005/2255* (2013.01)
(58) Field of Classification Search
  CPC ....... A61B 1/0669; A61B 1/07; A61B 1/0638; G06T 7/586; G06T 2207/10048; G06T 2207/10068; G06T 2207/10152; G06T 2207/20224; G06T 2207/30101; G06T 5/50; H04N 5/2256; H04N 2005/2255
  See application file for complete search history.

(56) References Cited

U.S. PATENT DOCUMENTS

| | | | |
|---|---|---|---|
| 2002/0165456 A1* | 11/2002 | Canpolat | A61B 5/444 600/473 |
| 2010/0048995 A1 | 2/2010 | Suijver et al. | |
| 2010/0195078 A1 | 8/2010 | Horiuchi et al. | |
| 2010/0240953 A1 | 9/2010 | Murakami | |
| 2010/0245551 A1 | 9/2010 | Morita | |
| 2011/0263955 A1 | 10/2011 | Narita et al. | |
| 2012/0123205 A1 | 5/2012 | Nie et al. | |
| 2012/0302847 A1 | 11/2012 | Ozawa et al. | |
| 2012/0327205 A1 | 12/2012 | Takahashi | |
| 2013/0270421 A1 | 10/2013 | Kanamori et al. | |
| 2014/0052005 A1* | 2/2014 | Yokota | A61B 5/1076 600/477 |
| 2014/0092227 A1 | 4/2014 | Kanamori et al. | |
| 2014/0267657 A1 | 9/2014 | Takei et al. | |
| 2015/0022647 A1* | 1/2015 | Takei | A61B 1/00186 348/70 |
| 2015/0238089 A1 | 8/2015 | Fujinuma et al. | |
| 2015/0320296 A1 | 11/2015 | Morita | |
| 2016/0041334 A1 | 2/2016 | Sulkier et al. | |
| 2016/0278678 A1* | 9/2016 | Valdes | A61B 1/00009 |
| 2016/0334340 A1 | 11/2016 | Ollivier et al. | |
| 2017/0006202 A1 | 1/2017 | Otani et al. | |
| 2017/0098301 A1 | 4/2017 | Ikemoto et al. | |
| 2017/0231480 A1 | 8/2017 | Yamazaki | |
| 2018/0164221 A1 | 6/2018 | Singh et al. | |
| 2020/0099844 A1 | 3/2020 | Shinji et al. | |
| 2020/0099845 A1 | 3/2020 | Matsumoto et al. | |
| 2020/0100650 A1 | 4/2020 | Oka | |

FOREIGN PATENT DOCUMENTS

| | | |
|---|---|---|
| EP | 2526854 A1 | 11/2012 |
| EP | 2979607 A1 | 2/2016 |
| EP | 3075301 A1 | 10/2016 |
| EP | 3202306 A1 | 8/2017 |
| JP | 2009-536066 A | 10/2009 |
| JP | 2010-213992 A | 9/2010 |
| JP | 2010-227256 A | 10/2010 |
| JP | 2012-239816 A | 12/2012 |
| JP | 2014-18439 A | 2/2014 |
| JP | 2014-188222 A | 10/2014 |
| JP | 2015-077415 A | 4/2015 |
| JP | 2015-231498 | 12/2015 |
| JP | 2016-49370 A | 4/2016 |
| JP | 2016-174836 A | 10/2016 |
| JP | 2016-198304 A | 12/2016 |
| JP | 2016-200418 A | 12/2016 |
| JP | 2016-209466 A | 12/2016 |
| JP | 2017-042629 A | 3/2017 |
| WO | WO 2007/132378 A2 | 11/2007 |
| WO | WO 2011/080996 A1 | 7/2011 |
| WO | WO 2011/081141 A1 | 7/2011 |
| WO | WO 2015/016013 A1 | 2/2015 |
| WO | WO 2016/151903 A1 | 9/2016 |
| WO | WO 2016/181720 A1 | 11/2016 |
| WO | WO 2018/229831 A1 | 12/2018 |
| WO | WO 2018/229832 A1 | 12/2018 |
| WO | WO 2018/229833 A1 | 12/2018 |

OTHER PUBLICATIONS

International Search Report dated Aug. 22, 2017 issued in PCT/JP2017/021661.
International Search Report dated Aug. 15, 2017 issued in PCT/JP2017/021664.
International Search Report dated Aug. 22, 2017 issued in PCT/JP2017/021665.
International Search Report dated Aug. 22, 2017 issued in PCT/JP2017/021667.
Shree K. Nayar et al., "Fast separation of direct and global components of a scene using high frequency illumination", ACM Transactions on Graphics (Jul. 3, 2006), vol. 25, Issue 3, pp. 935-944, cited in ISR.
T. Takatani et al., "Decomposition of Reflected and Scattered Lights by Multiple Weighted Measurements", 14th Symposium on Image Recognition and Understanding (MIRU2011) (Jul. 2011).
K. Tanaka et al., "Adaptive Frequency Selection under Parallel High-frequency Illumination", 16th Symposium on Image Recognition and Understanding (MIRU2013), Collection of Extended Abstract,Information Processing Society of Japan, Yoshiki Shimotsuma, SS2-33.
T. Takatani et al.,"Decomposition of Reflected and Scattered Lights by Multiple Weighted Measurements", IPSJ SIG Technical Report (CD-ROM), vol. 2011, No. 1, ROMBUNNO.CVIM-177, No. 12, ISSN 2186-2583.
International Search Report dated Jul. 24, 2018 issued in International Application No. PCT/JP2018/021590, together with a partial English language translation.
International Search Report dated Jul. 24, 2018 issued in International Application No. PCT/JP2018/021597, together with a partial English language translation.
Office Action dated Dec. 11, 2020 received in U.S. Appl. No. 16/691,961.

* cited by examiner

FIG. 4D
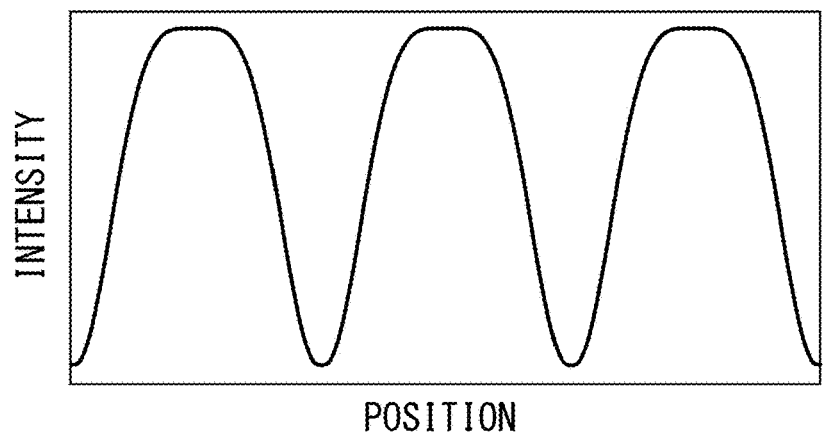
FIG4. E
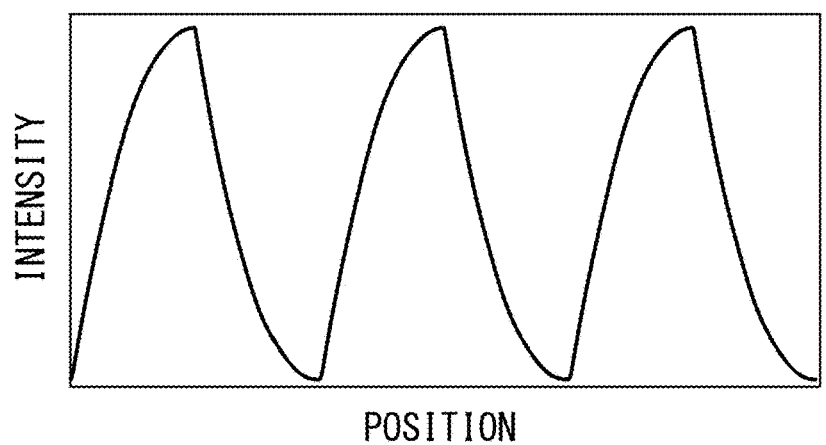
FIG. 4F
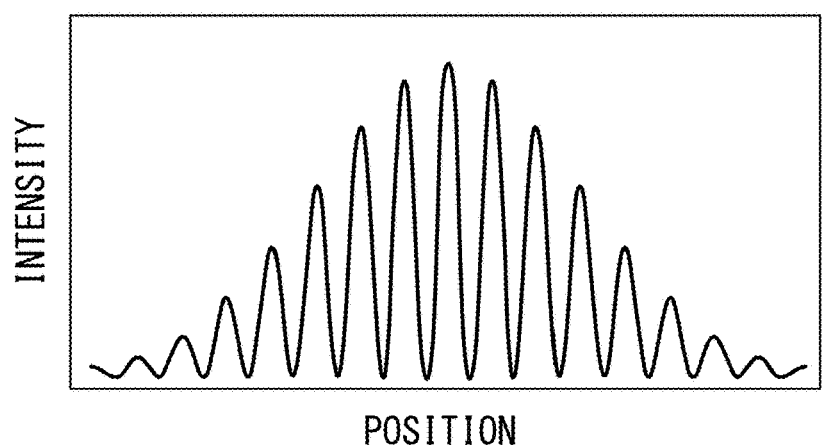

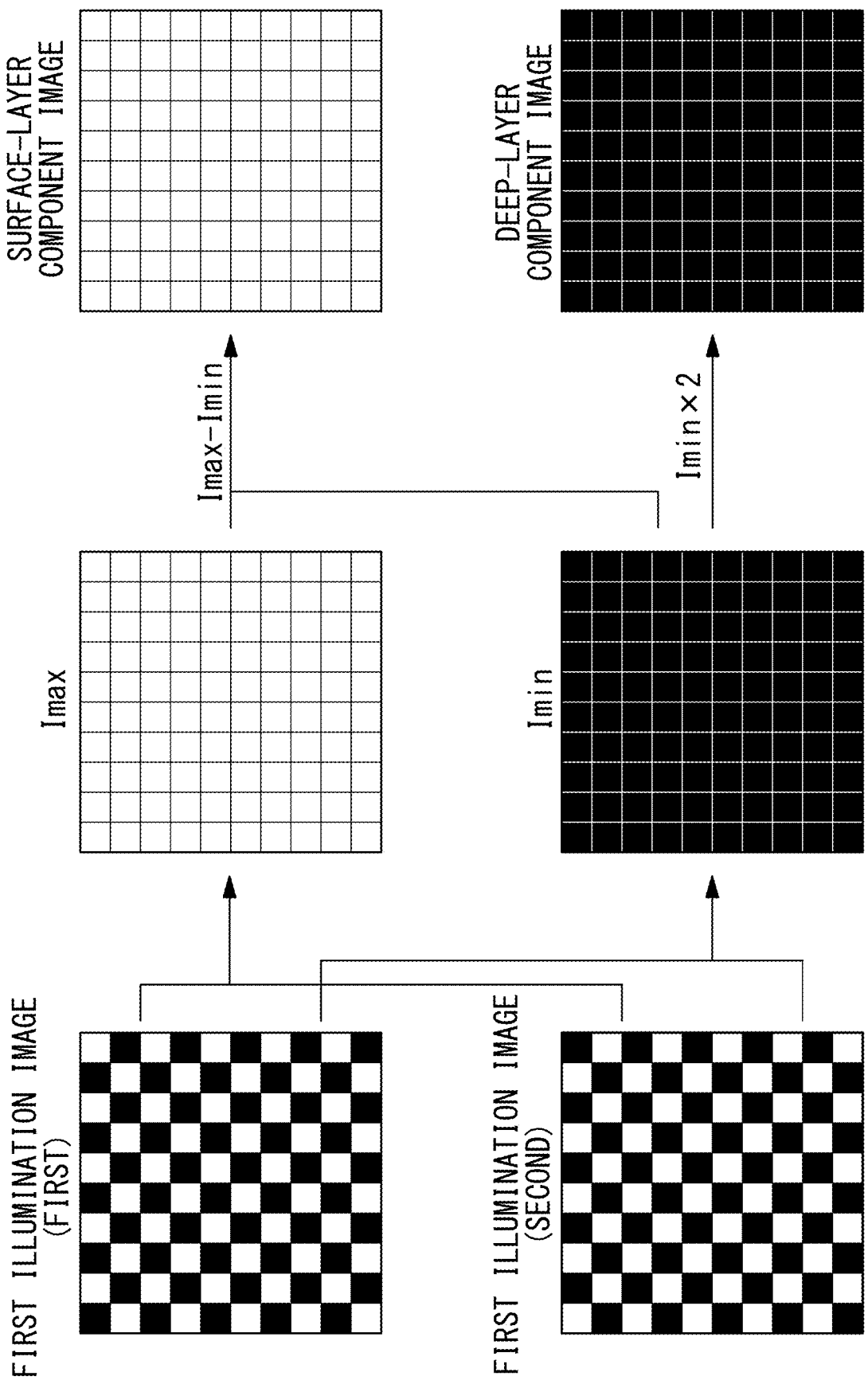

ENDOSCOPE SYSTEM

CROSS-REFERENCE TO RELATED APPLICATIONS

This is a continuation of International Application PCT/JP2017/021667, with an international filing date of Jun. 12, 2017, which is hereby incorporated by reference herein in its entirety.

TECHNICAL FIELD

The present invention relates to an endoscope system.

BACKGROUND ART

Light generated from an illuminated object contains a plurality of different components such as such as specularly reflected light, diffuse reflected light, and scattered light. A technology for separating information about the surface of the object and information about the inside of the object by separating such components contained in an image of the object by using a high-frequency pattern projection method in which structured illumination light having a striped bright-dark pattern is used has been proposed (for example, refer to NPL 1).

CITATION LIST

Non Patent Literature

{NPL 1} "Analysis of reflected/scattered light by multiple weighting measurement", Takeshi TAKATANI and three others, Fourteenth Meeting on Image Recognition and Understanding (MIRU 2011), July 2011

SUMMARY OF INVENTION

One aspect of the present invention provides an endoscope system that includes: a first illumination unit that emits, toward a subject, first illumination light that is for imaging two sets of image information about the subject at different depths; a second illumination unit that emits second illumination light toward the subject; an imaging unit that images a first illumination image of the subject illuminated with the first illumination light and a second illumination image of the subject illuminated with the second illumination light; a separation processing unit that separates the two sets of image information from the first illumination image; and a separated-image creating unit that processes the second illumination image using the two sets of image information to create two separated images respectively containing a lot of information about the subject at the different depths. The first illumination light is light of a different wavelength band from the second illumination light. The first illumination unit and the second illumination unit simultaneously emit the first illumination light and the second illumination light. The imaging unit captures images of the subject illuminated with the first illumination light and the second illumination light to simultaneously image the first illumination image and the second illumination image.

BRIEF DESCRIPTION OF DRAWINGS

FIG. 4D is a diagram illustrating another example of the spatial profile of the intensity of the first illumination light.

FIG. 4E is a diagram illustrating another example of the spatial profile of the intensity of the first illumination light.

FIG. 4F is a diagram illustrating another example of the spatial profile of the intensity of the first illumination light.

FIG. 6 is a diagram for explaining processing for creating a surface-layer component image and a deep-layer component image in a separation processing unit.

DESCRIPTION OF EMBODIMENTS

Figure 1:
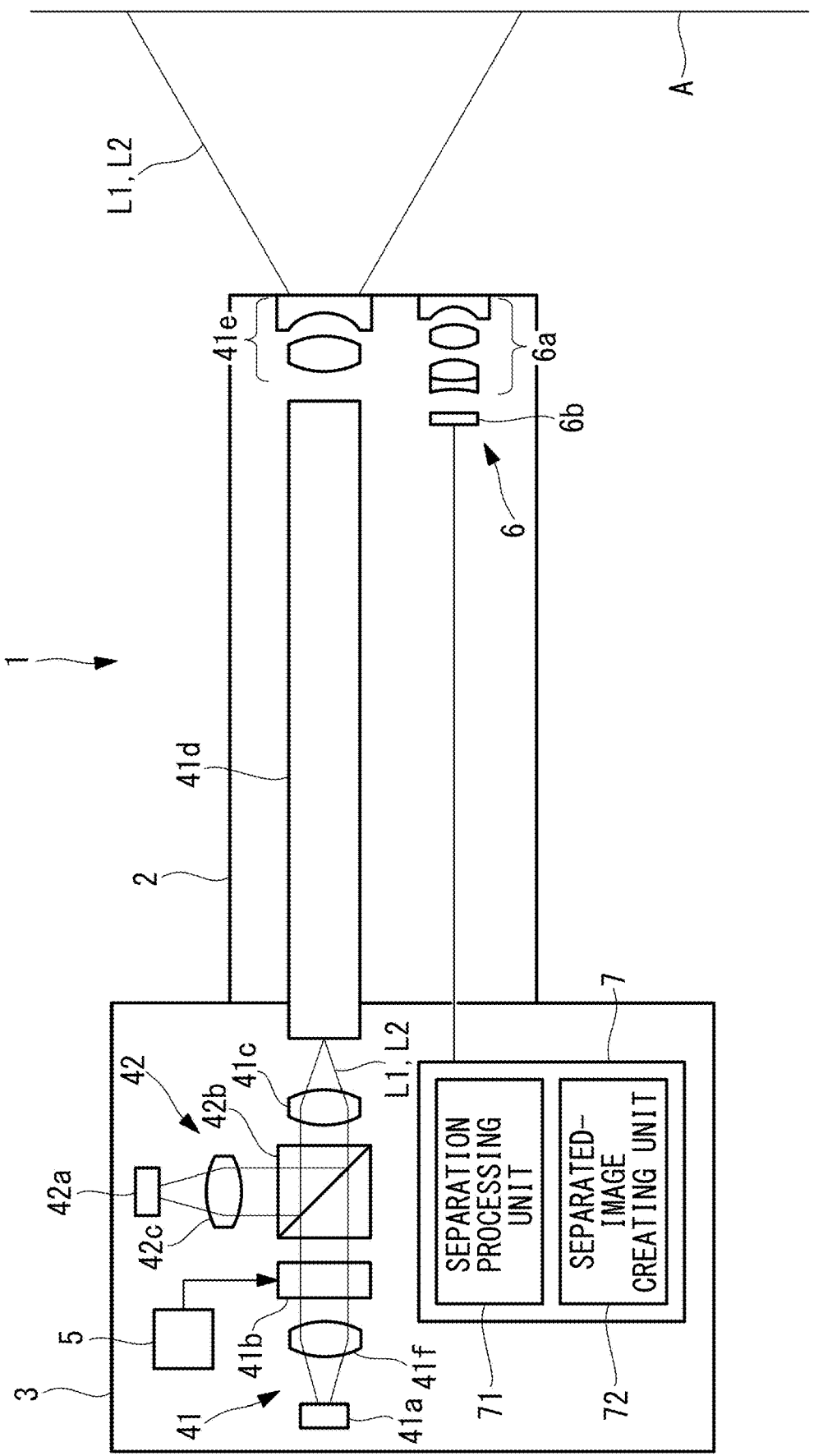
FIG. 1 is an overall configuration diagram of an endoscope system according to an embodiment of the present invention.

Hereafter, an endoscope system 1 according to an embodiment of the present invention will be described while referring to the drawings.

As illustrated in FIG. 1, the endoscope system 1 according to this embodiment includes an endoscope 2 that is for observing the inside of a body and a body part 3 that is connected to a base end of the endoscope 2.

The endoscope system 1 further includes: a first illumination unit 41 and a second illumination unit 42 that respectively emit infrared illumination light L1 and white second illumination light L2 from the distal end of the endoscope 2 towards biological tissue (subject) A inside the body; an intensity-distribution changing unit 5 that changes the intensity distribution of the first illumination light L1 over time; an imaging unit 6 that images first and second illumination images of the biological tissue A illuminated with the illumination light L1 and the illumination light L2; and an image processing unit 7 that creates two separated images containing information at different depths inside the biological tissue A by performing processing on the first and second illumination images imaged by the imaging unit 6.

Figure 2A:
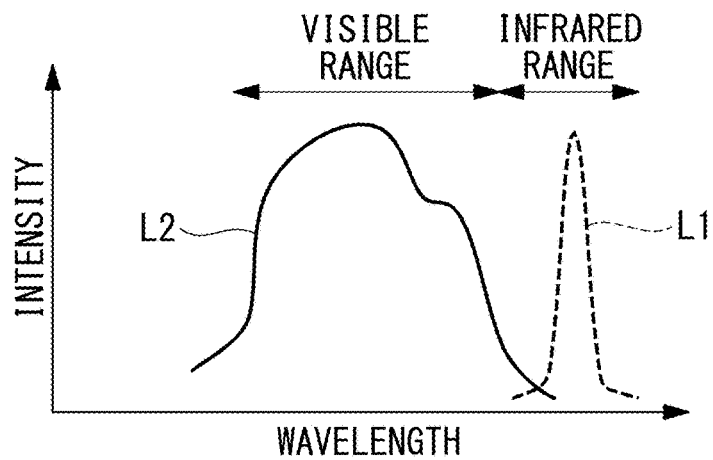
FIG. 2A is a diagram illustrating the wavelength bands of first illumination light and second illumination light.

FIG. 2A illustrates the wavelength band of the first illumination light L1 and the wavelength band of the second illumination light L2.

The first illumination unit 41 includes a light source 41a that outputs infrared light. The first illumination unit 41 generates, from the infrared light emitted from light source 41a, the first illumination light L1 having a spatially non-uniform intensity distribution in a light beam cross section perpendicular to the optical axis and emits the first illumination light L1 from a distal end surface of the endoscope 2 toward the biological tissue A. The first illumination light L1 will typically have an intensity gradient in which the brightness gradually decreases from the center of the light beam towards the periphery of the light beam. In addition to the overall intensity gradient of the cross section of the light beam, the first illumination light L1 has a structured bright-dark pattern in which a bright part having a high intensity and a dark part having a lower intensity than the bright part or having no intensity at all alternate in a repeating manner in the cross section of the light beam.

The first illumination unit 41 includes the light source 41a, a mask 41b, and a condenser lens 41c, which are provided in the body part 3, and an image guide fiber 41d and a projection lens 41e, which are provided in the endoscope 2.

The light source 41a is a semiconductor light source such as an LED or an LD.

The mask 41b is a liquid crystal element that can electrically control the light transmittance at each position within an incident region on which the infrared light from the light source 41a is incident, and a projection pattern is formed therein that corresponds to the bright-dark pattern and consists of light-transmitting regions through which the infrared light is allowed to pass and light-blocking regions where the infrared light is blocked. The infrared light output from the light source 41a is given a bright-dark pattern as a result of being transmitted through the mask 41b and the first illumination light L1 is thereby generated. The generated first illumination light L1 is collected at the incident end of the image guide fiber 41d by the condenser lens 41c, is guided by the image guide fiber 41d to the projection lens 41e provided at the distal end of the endoscope 2 while preserving the bright-dark pattern, and the first illumination light L1 is emitted as a diverging light beam from the projection lens 41e.

The second illumination unit 42 includes a light source 42a that outputs white light, and the second illumination unit 42 emits the white second illumination light L2 having a spatially substantially uniform intensity distribution in a light beam cross section perpendicular to the optical axis from the same position as the first illumination light L1 at the distal end of the endoscope 2 toward the biological tissue A.

The second illumination unit 42 includes, in the body part 3, the light source 42a and a beam splitter 42b that combines the second illumination light L2 output from the light source 42a and the first illumination light L1. The second illumination light L2, which has been combined with the first illumination light L1 by the beam splitter 42b, passes along the same optical path as the first illumination light L1 and is radiated onto the biological tissue A. Symbols 41f and 42c denote collimator lenses that convert light emitted from the light sources 41a and 42a into parallel light beams.

The light source 42a is a semiconductor light source such as an LED or an LD or is a lamp light source such as a xenon lamp. White light may be generated by combining red light, green light, and blue light output from a plurality of light sources 42a.

The first illumination unit 41 and the second illumination unit 42 are controlled by a control device, which is not illustrated, provided in the body part 3 so that the first illumination unit 41 and the second illumination unit 42 simultaneously emit the first illumination light L1 and the second illumination light L2.

The intensity-distribution changing unit 5 is a control element that controls the light transmittance at each position within an incident region of the mask 41b and causes the intensity distribution of the first illumination light L1 to change over time such that the bright parts and the dark parts are swapped with each other in the cross section of the light beam. As a result, bright parts and dark parts are sequentially projected at each position within the range in which the first illumination light L1 is radiated onto a surface B of the biological tissue A.

FIGS. 3A to 3F illustrate examples of the bright-dark pattern of the first illumination light L1 and how the intensity distribution changes over time. In FIGS. 3A to 3F, the white regions represent the bright parts and the black regions represent the dark parts.

Figure 3A:
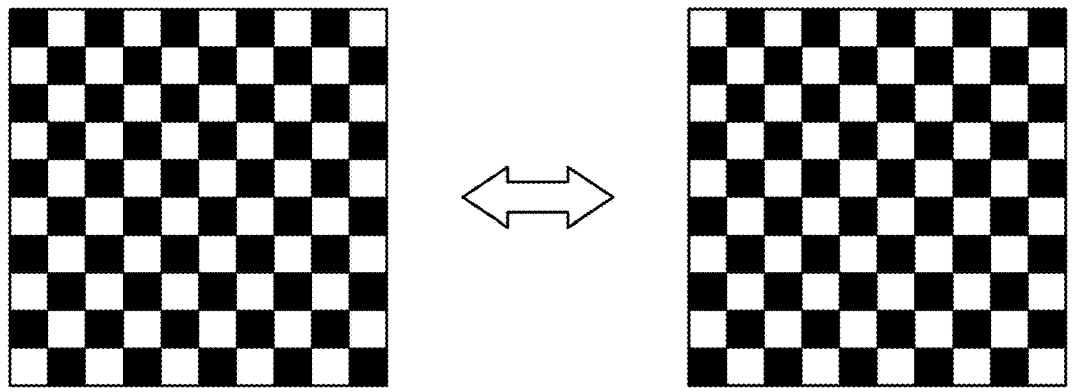
FIG. 3A is a diagram illustrating an example of the intensity distribution of the first illumination light and how the intensity distribution of the first illumination light changes over time.

The bright-dark patterns in FIG. 3A are checkered patterns in which square bright parts and square dark parts alternate in a repeating manner in two perpendicular directions.

Figure 3B:
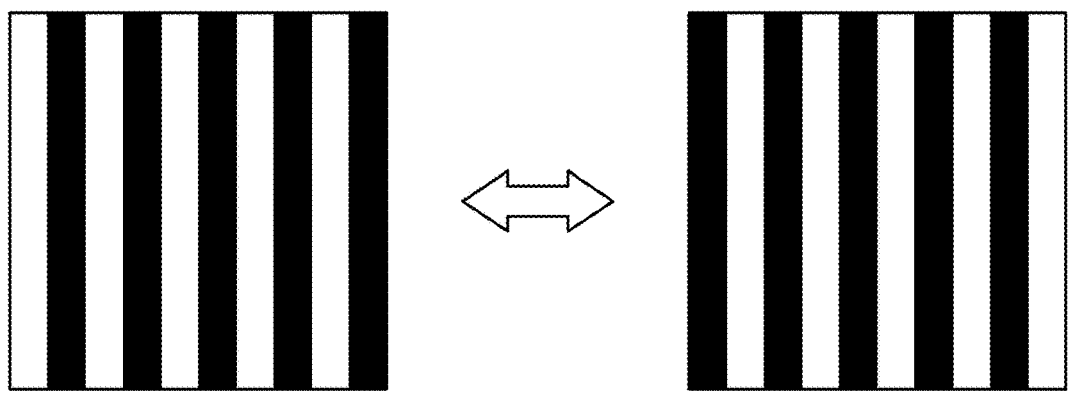
FIG. 3B is a diagram illustrating another example of the intensity distribution of the first illumination light and how the intensity distribution of the first illumination light changes over time.
Figure 3C:
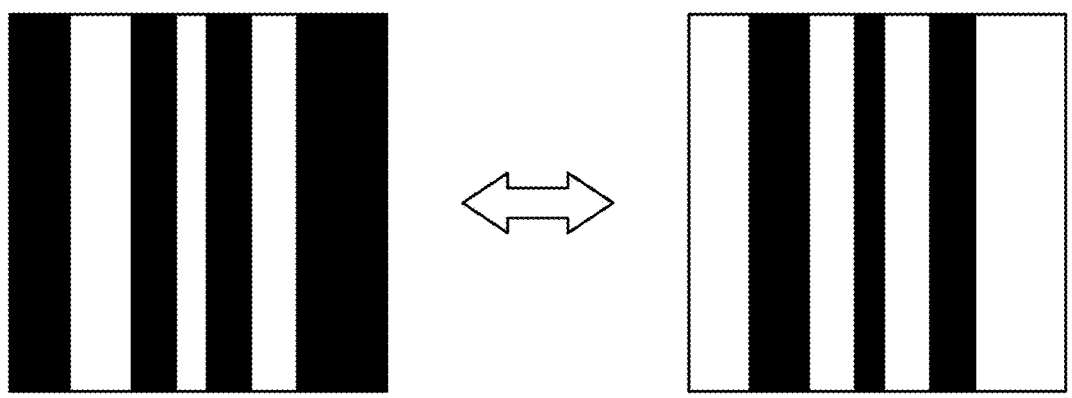
FIG. 3C is a diagram illustrating another example of the intensity distribution of the first illumination light and how the intensity distribution of the first illumination light changes over time.

The bright-dark patterns in FIGS. 3B and 3C are striped patterns in which straight band-shaped bright parts and dark parts alternate in a repeating manner in only a width direction, which is perpendicular to the length directions of the bright parts and dark parts. The spatial period of the bright parts and dark parts in the strip patterns may be constant as illustrated in FIG. 3B, or may be vary, as illustrated in FIG. 3C.

Figure 3D:
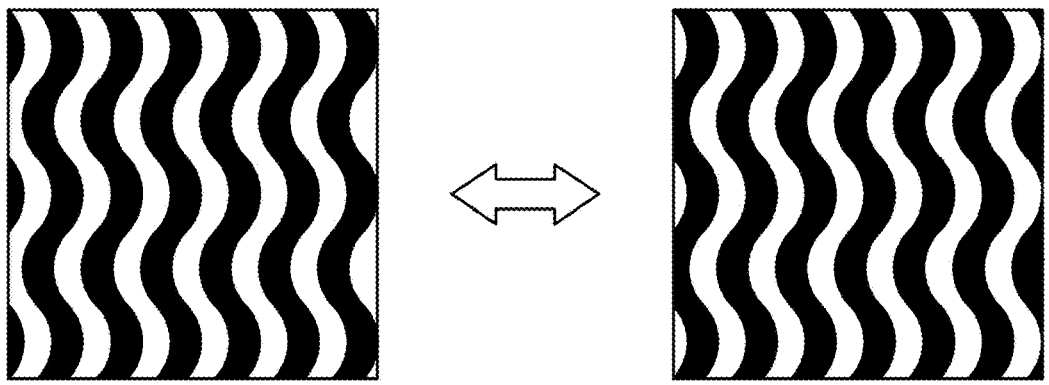
FIG. 3D is a diagram illustrating another example of the intensity distribution of the first illumination light and how the intensity distribution of the first illumination light changes over time.

The bright-dark patterns in FIG. 3D are striped patterns in which wave-like band-shaped bright parts and dark parts alternate in a repeating manner in only the width direction, which is perpendicular to the length directions of the bright parts and dark parts.

Figure 3E:
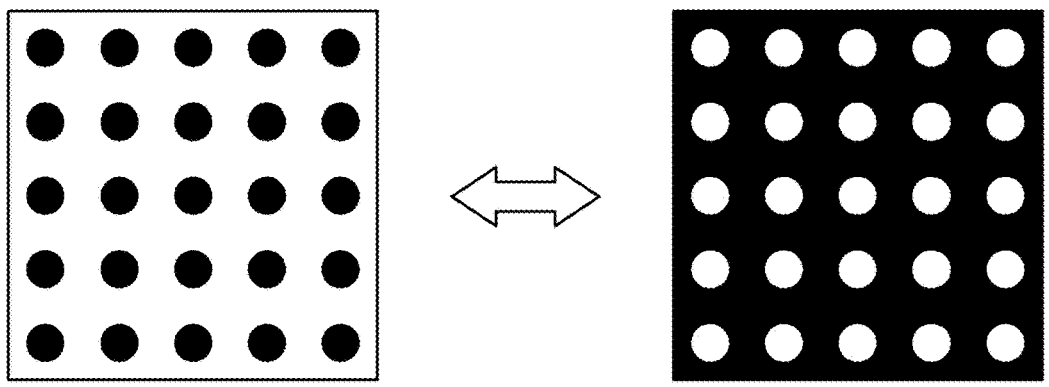
FIG. 3E is a diagram illustrating another example of the intensity distribution of the first illumination light and how the intensity distribution of the first illumination light changes over time.

The bright-dark patterns in FIG. 3E are dot patterns in which one out of the bright parts and the dark parts consists of circles and the other forms the background.

Figure 3F:
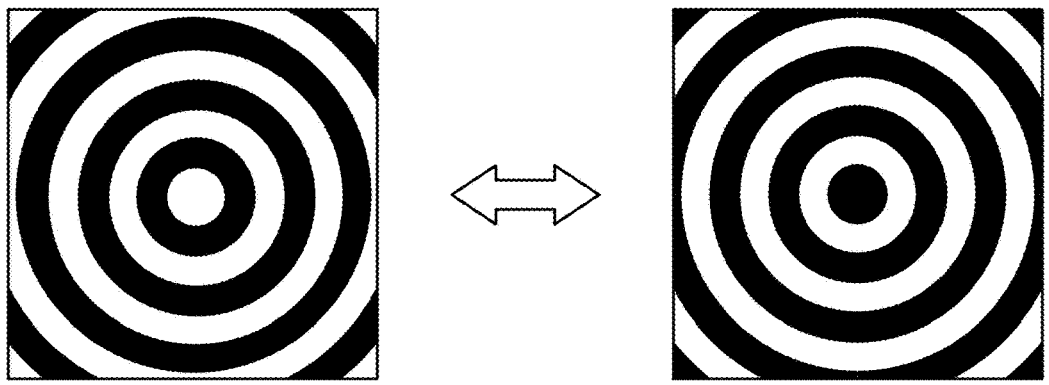
FIG. 3F is a diagram illustrating another example of the intensity distribution of the first illumination light and how the intensity distribution of the first illumination light changes over time.

The bright-dark patterns in FIG. 3F are concentric circle patterns in which circular band-shaped bright parts and dark parts alternate in a repeating manner in a radial direction.

Figure 4A:
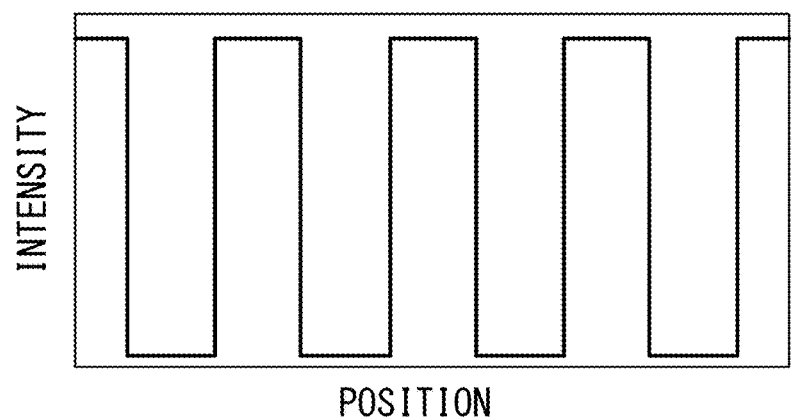
FIG. 4A is a diagram illustrating an example of the spatial profile of the intensity of the first illumination light.
Figure 4B:
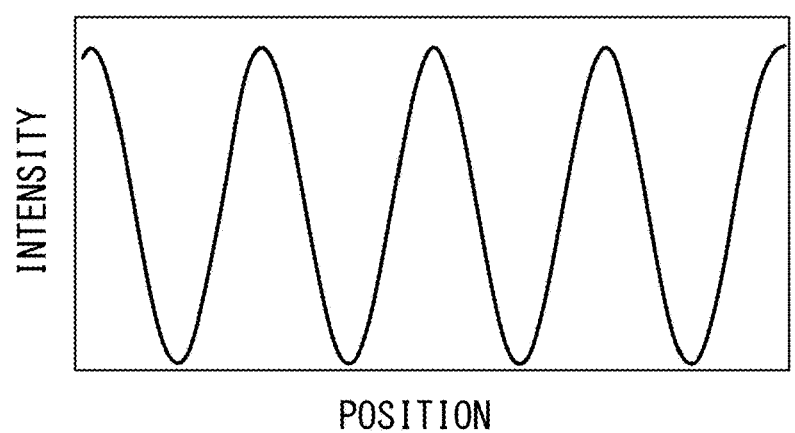
FIG. 4B is a diagram illustrating another example of the spatial profile of the intensity of the first illumination light.
Figure 4C:
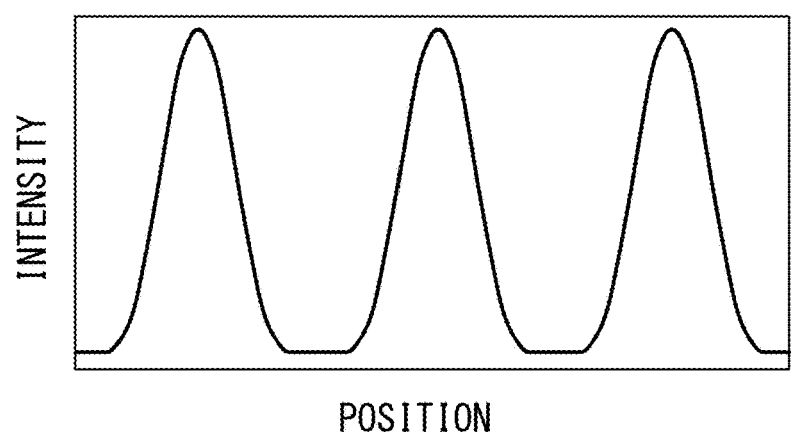
FIG. 4C is a diagram illustrating another example of the spatial profile of the intensity of the first illumination light.

FIGS. 4A to 4F illustrate examples of intensity profiles that represents the spatial changes in intensity I between the bright parts and dark parts in the bright-dark patterns in FIGS. 3A to 3F. The horizontal axis represents position X. The intensity profile may have a rectangular wave shape, as illustrated in FIG. 4A, may have a sinusoidal shape, as illustrated in FIG. 4B, may have an intermediate shape that is in between a rectangular wave shape and a sinusoidal shape, as illustrated in FIGS. 4C and 4D, or may have a non-symmetrical wave shape, as illustrated in FIG. 4E. As illustrated in FIG. 4E, the intensity profile may be highest at the center of the first illumination light L1 and may decrease overall from the center toward the peripheries. The period of the bright parts and the dark parts may be the interval between a bright part and the adjacent bright part in FIGS. 4A to 4E.

Figure 5A:
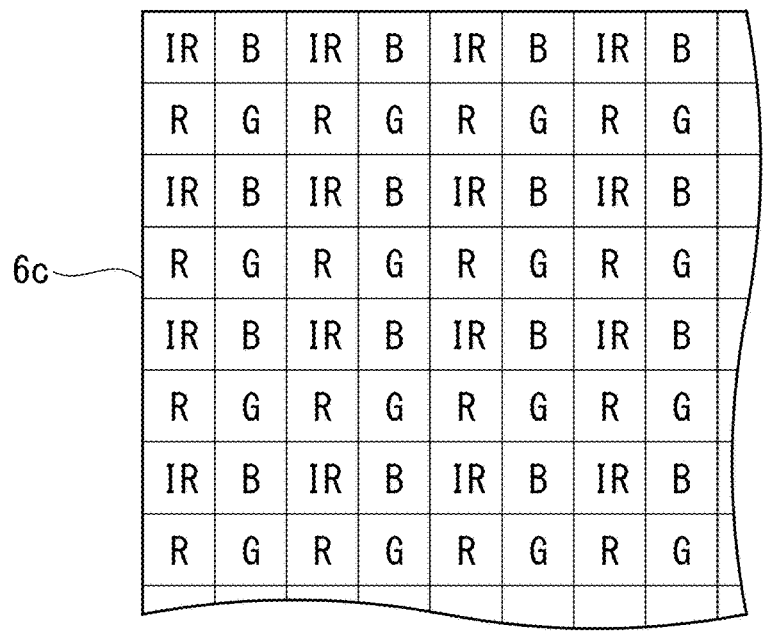
FIG. 5A is a diagram illustrating an example of an imaging element provided in an imaging unit.
Figure 5B:
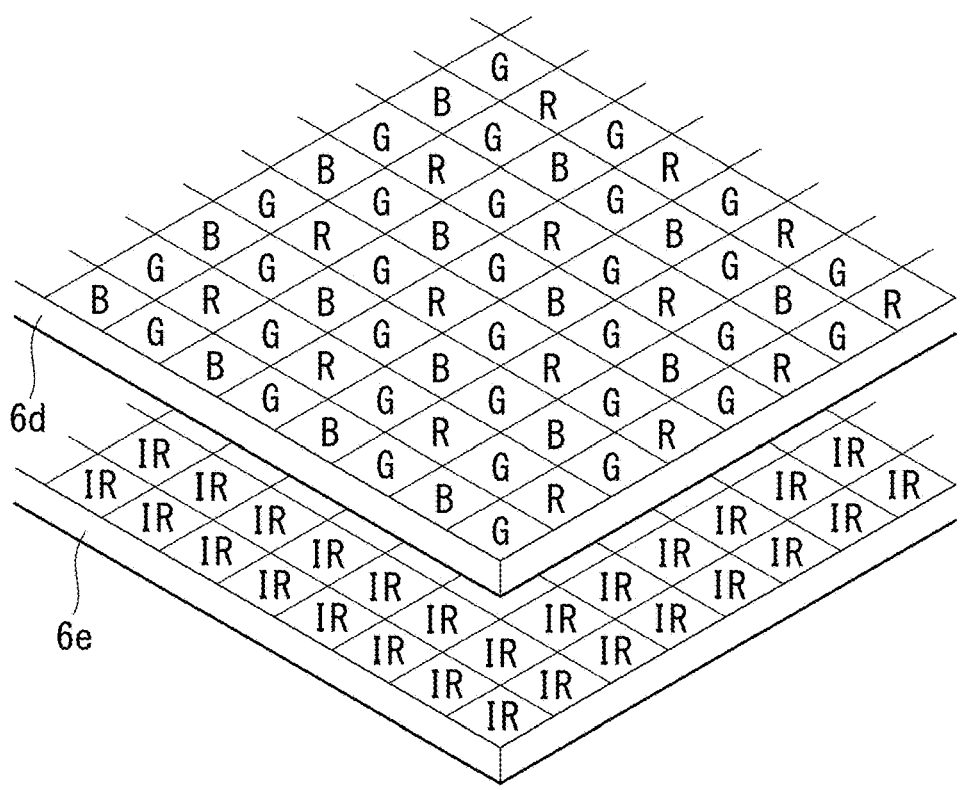
FIG. 5B is a diagram illustrating another example of an imaging element provided in an imaging unit.

The imaging unit 6 includes an imaging lens 6a that is provided at the distal end of the endoscope 2 and collects light from the biological tissue A and an imaging element 6b that captures an image of the biological tissue A formed by the imaging lens 6a. The imaging element 6b is configured to be able to spatially separate and simultaneously capture infrared light and white light. For example, as illustrated in FIG. 5A, an imaging element including a color filter array 6c consisting of an array of red (R), green (G), blue (B), and infrared (IR) color filters is used as the imaging element 6b. Alternatively, as illustrated in FIG. 5B, an imaging element in which are stacked a first substrate 6d that is for capturing white light and in which white light sensors are formed on an imaging surface thereof and a second substrate 6e that is for capturing infrared light that has passed through the first substrate 6d and in which infrared light sensors are formed on an imaging surface thereof is used as the imaging element 6b.

The imaging unit 6 performs image capturing when the biological tissue A is irradiated with both the first illumination light L1 and the second illumination light L2, and simultaneously images a first illumination image of the biological tissue A illuminated with the first illumination light L1 and a second illumination image of the biological tissue A illuminated with the second illumination light L2. The first illumination image and the second illumination image imaged by the imaging element 6b are transmitted from the imaging element 6b to the image processing unit 7.

The intensity distribution of the first illumination light L1 radiated onto the biological tissue A is changed over time by the intensity-distribution changing unit 5 as illustrated in FIGS. 3A to 3F. The imaging element 6b performs image capturing at two time points at which the biological tissue A is irradiated with beams of the first illumination light L1 in which the bright parts and the dark parts have been reversed with respect to each other, and as a result, as illustrated in FIG. 6, the imaging element 6b images two first illumination images in which the projection regions of the bright parts and the projection regions of the dark parts are reversed with respect to each other and in which the projection regions of the bright parts and the projection regions of the dark parts complement each other. In the first illumination images in FIG. 6, the white regions represent the projection regions of the bright parts and the black regions represent the projection regions of the dark parts. Therefore, the operations of the intensity-distribution changing unit 5 and the imaging element 6b are controlled by the control device so that the timing at which the intensity distribution is changed by the intensity-distribution changing unit 5 and the timing at which an image is captured by the imaging element 6b are synchronized with each other.

The image processing unit 7 includes a separation processing unit (separation processor) 71 that separates a surface-layer component image (image information) and a deep-layer component image (image information) from the two first illumination images and a separated-image creating unit 72 that creates a surface layer image (separated image) and a deep layer image (separated image) by performing processing on the second illumination image using the surface-layer component image and the deep-layer component image.

FIG. 6 illustrates image processing performed by the separation processing unit 71. For the pixels at each position in the two first illumination images, intensity values Imax when the bright parts are projected and intensity values Imin when the dark parts are projected are imaged. As illustrated in FIG. 6, the separation processing unit 71 creates a deep-layer component image that contains a lot of information about a deep layer D of the biological tissue A from the intensity values Imin of the two first illumination images and creates a surface-layer component image that contains a lot of information about the surface B and a surface layer C of the biological tissue A from the intensity values Imin and the intensity values Imax of the two first illumination images.

Figure 7:
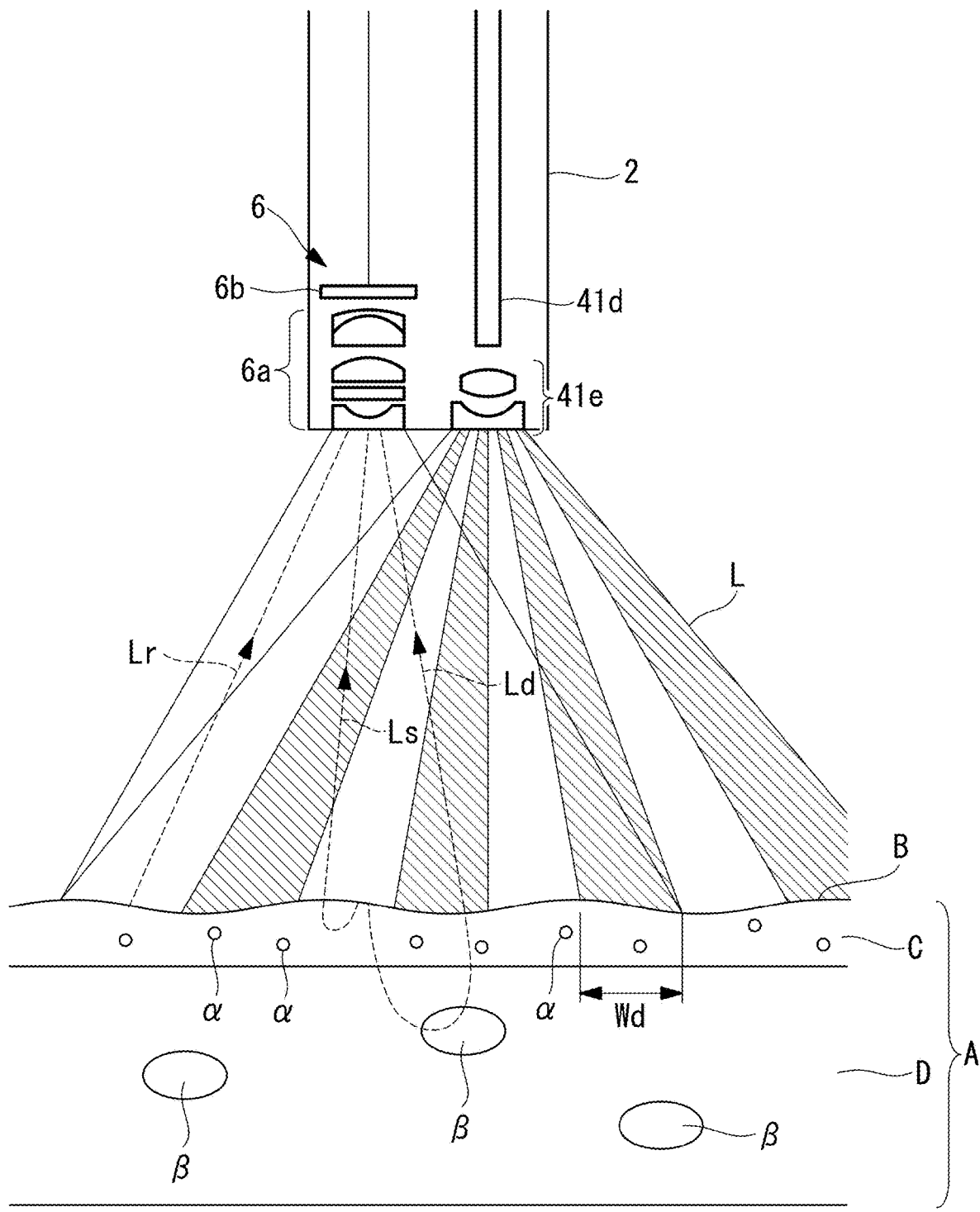
FIG. 7 is a diagram for explaining the relationship between specularly reflected light, surface scattered light, and internally scattered light generated in biological tissue as a result of irradiation with the first illumination light and the positions at which these types of light are generated.

The biological tissue A is a scattering body, and as illustrated in FIG. 7, structures α, such as capillary vessels, are included in the surface layer C, which extends from the surface B to a depth of several tens of μm, and structures β, such as thick blood vessels, are included in the deep layer D, which is deeper than the surface layer C. When the biological tissue A is irradiated with the first illumination light L1 having a bright-dark pattern, specularly reflected (specular) light Lr, surface scattered light Ls, and internally scattered light Ld are generated by the biological tissue A.

The specular light Lr is reflected light, among the first illumination light L1, that has been specularly reflected by the surface B of the biological tissue A and is generated in the projection regions of the bright parts.

The surface scattered light Ls is scattered light, among the first illumination light L1, that has entered the inside of the biological tissue A from the projection regions of the bright parts, passed through the surface layer C while undergoing repeated scattering, and then been emitted from the surface B. Almost all the surface scattered light Ls is emitted from the projection regions of the bright parts.

The internally scattered light Ld is scattered light, among the first illumination light L1, that has entered the inside of the biological tissue A from the projection regions of the bright parts, passed through the deep layer D while undergoing repeated scattering, and then been emitted from the surface B. Some of the internally scattered light Ld is emitted from the projection regions of the bright parts and the remainder of the internally scattered light Ld propagates to the projection regions of the dark parts and is emitted from the projection regions of the dark parts.

Thus, the intensity values Imin of the projection regions of the dark parts within the two first illumination images are mainly based on the internally scattered light Ld and mainly include information about the deep layer D. On the other hand, the intensity values Imax of the projection regions of the bright parts within the two first illumination images are based on the specular light Lr, the surface scattered light Ls, and the internally scattered light Ld and include information about the surface B, the surface layer C, and the deep layer D.

Figure 8:
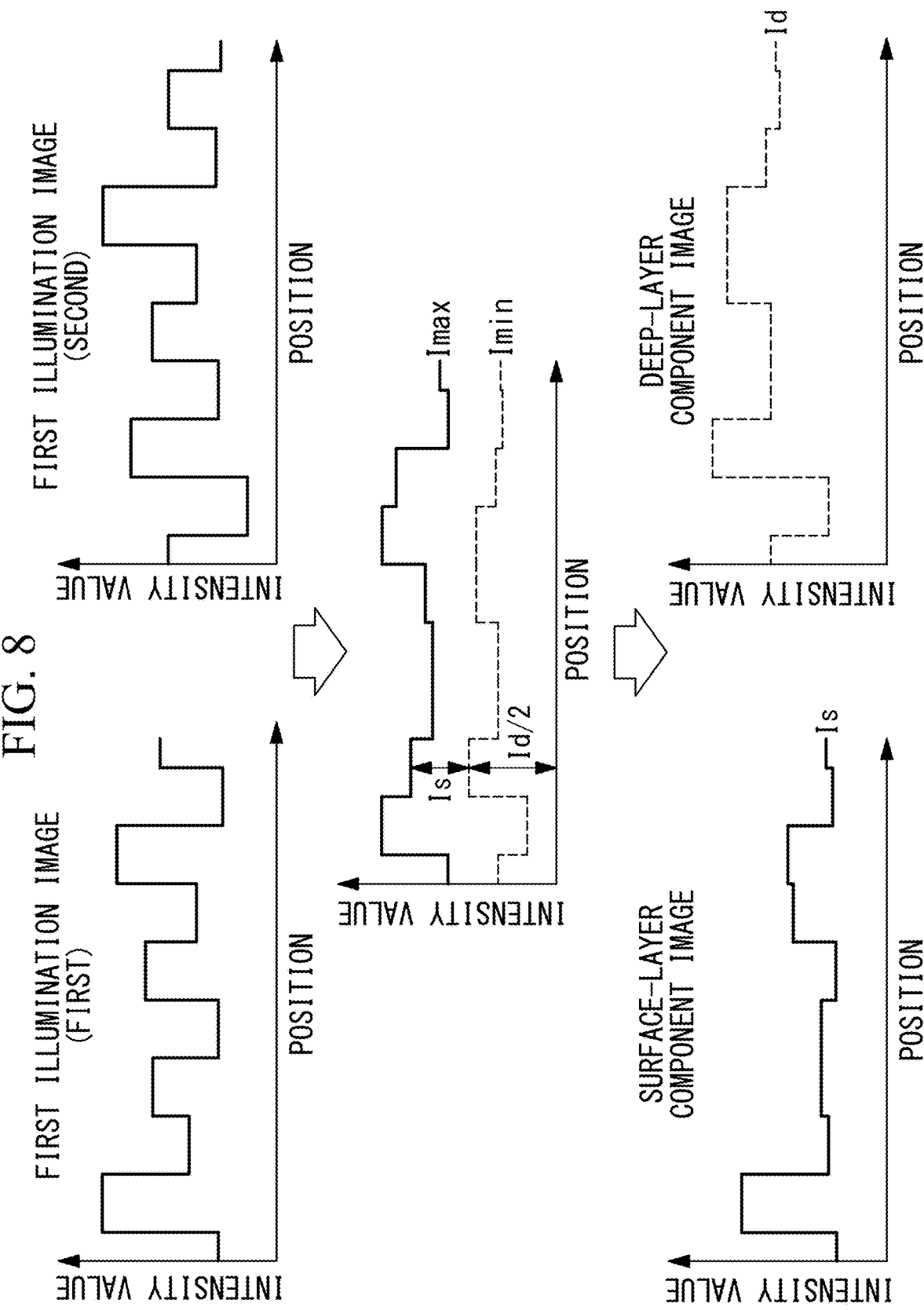
FIG. 8 is a diagram for explaining method for creating a surface-layer component image and a deep-layer component image in a separation processing unit.

FIG. 8 illustrates a specific method with which a surface-layer component image and a deep-layer component image are created by the separation processing unit 71. As illustrated in FIG. 8, the two first illumination images have a brightness distribution in which the intensity value is high in the pixels corresponding to the projection regions of the bright parts and the intensity value is low in the pixels corresponding to the projection regions of the dark parts. In FIG. 8, for ease of explanation, the first illumination light L1 has a bright-dark pattern in which a bright part and a dark part repeat at a constant period, as in the bright-dark pattern of FIG. 3A or FIG. 3B, and an intensity profile is illustrated for a case where the boundaries between pixels of the image and the boundaries between the bright parts and the dark parts in the bright-dark pattern coincide with each other (that is, one bright part or dark part corresponds to one pixel).

As described above, two intensity values Imax and Imin are obtained for each pixel from the two first illumination images. For each pixel, the separation processing unit 71 determines the higher intensity value as the intensity value Imax and the lower intensity value as the intensity value Imin. Next, the separation processing unit 71 calculates an intensity value Is of each pixel of the surface-layer component image and an intensity value Id of each pixel of the deep-layer component image using the following formula, and creates a surface-layer component image having the intensity values Is and a deep-layer component image having the intensity values Id.

$Is = I\max - I\min$ $Id = I\min \times 2$

Thus, a deep-layer component image having intensity values Imin mainly including information about the deep layer D is created. A surface-layer component image having intensity values Is mainly including information about the surface B and the surface layer C is created by subtracting the intensity values Imin from the intensity values Imax in order to remove the information about the deep layer D.

Figure 9:
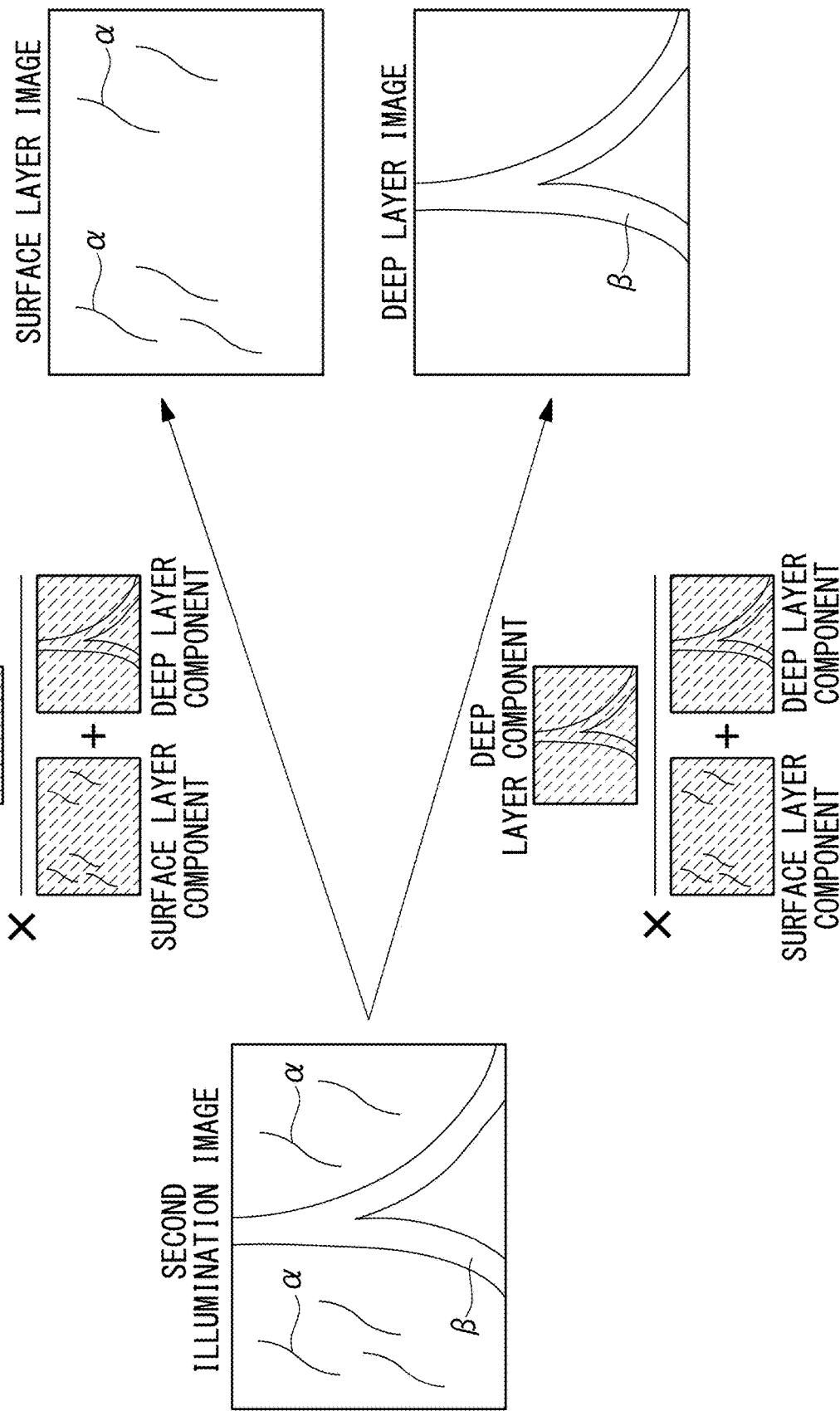
FIG. 9 is a diagram for explaining processing for creating a surface layer image and a deep layer image in a separated-image creating unit.

As illustrated in FIG. 9, the separated-image creating unit 72 creates a surface layer image on the basis of formula (a) below and creates a deep layer image on the basis of formula (b) below.

Surface layer image=second illumination image× surface-layer component image/(surface-layer component image+deep-layer component image)    (a)

Deep layer image=second illumination image×deep-layer component image(surface-layer component image+deep-layer component image)    (b)

In other words, the separated-image creating unit 72 creates a surface layer image by calculating the ratio of the surface-layer component image to the sum of the surface-layer component image and the deep-layer component image, and multiplying the calculated ratio by the second illumination image. The separated-image creating unit 72 creates a deep layer image by calculating the ratio of the deep-layer component image to the sum of the surface-layer component image and the deep-layer component image, and multiplying the calculated ratio by the second illumination image.

The surface layer image and the deep layer image created by the separated-image creating unit 72 are output from the body part 3 to a display device (not illustrated), which is connected to the body part 3, and are displayed on the display device.

The image processing unit 7 is implemented as an image-processing program that is executed by a computer, for example. In other words, the body part 3 includes a central processing unit (CPU), a main storage device such as a RAM, and an auxiliary storage device such as a hard disk drive, and an image processing program for causing the CPU to execute the above-described processing using the image processing unit 7 is stored in the auxiliary storage device. The image processing program is loaded from the auxiliary storage device into the main storage device and the CPU executes processing in accordance with the image processing program, and thereby the above-described functions of the image processing unit 7 are realized.

When the second illumination light L2, which is normal white light having a spatially substantially uniform intensity distribution, is radiated onto the biological tissue A, the specular light Lr, the surface scattered light Ls, and the internally scattered light Ld are incident on the imaging unit 6 in a state of being superimposed with each other. Therefore, the structures $\alpha$, such as capillary vessels, in the surface layer C extending from the surface B to a depth of several tens of μm and the structures $\beta$, such as thick blood vessels, in the deep layer D are both displayed in the second illumination image obtained by image capturing the biological tissue A illuminated with the second illumination light L2.

In contrast, when the first illumination light L1 having a bright-dark pattern is radiated onto the biological tissue A, the internally scattered light Ld, which contains a lot of information about the deep layer D, is spatially separated from the specular light Lr and the surface scattered light Ls containing information about the surface B and the surface layer C, and the first illumination image in which the region where information about the deep layer D is dominant is spatially separated from the region containing a lot of information about the surface B and the surface layer C is obtained. A surface-layer component image that mainly contains information about the surface B and the surface layer C and in which images of the structures $\alpha$ are emphasized and a deep-layer component image that mainly contains information about the deep layer D and in which images of the structures $\beta$ are emphasized can be separated from the first illumination image.

It may be difficult to ensure a sufficient amount of light for the structured first illumination light L1 due to design limitations and so forth of the first illumination unit 41, whereas it is easy to ensure that there is a sufficient amount of light for the second illumination light L2, which is normal white light, and a bright second illumination image can be obtained. This embodiment has an advantage in that a bright surface layer image and a bright deep layer image can be created by creating a surface layer image and a deep layer image by correcting a bright second illumination image using a surface-layer component image and a deep-layer component image.

The first illumination image and the second illumination image can be simultaneously imaged by using first illumination light L1 having a wavelength band that is different from the wavelength band of the second illumination light L2. Thus, compared with a case where the first illumination image and the second illumination image are sequentially imaged by sequentially radiating the first illumination light L1 and the second illumination light L2 onto the biological tissue A, there is an advantage in that a high frame rate can be achieved for the surface layer image and the deep layer image.

Furthermore, noise arising from specular light within the first illumination image can be prevented from being generated in the surface layer image by emitting the first illumination light L1 and the second illumination light L2 from identical positions at the distal end of the endoscope 2.

In the case where the first illumination light L1 and the second illumination light L2 are emitted toward the biological tissue A from different positions, deviations are generated between the positions of specular light within the first illumination image and the positions of specular light within the second illumination image. When first and second illumination images having different specular light positions are used to create a surface layer image and a deep layer image, white (i.e., high gradation value) spotted noise is generated in the surface layer image and black (i.e., low gradation value) spotted noise is generated in the deep layer image.

In contrast, in the case where the first illumination light L1 and the second illumination light L2 are emitted toward the biological tissue A from identical positions, the positions of specular light within the first illumination image and the positions of specular light within the second illumination image coincide with each other. Spotted noise is not generated in the surface layer image and the deep layer image when such a first illumination image and second illumination image are used.

The amount of information about the surface layer C in the surface layer image and the amount of information about the deep layer D in the deep layer image depend on the width Wd (refer to FIG. 7) of the dark parts on the surface B of the biological tissue A. Specifically, as the width Wd of the dark parts becomes larger, the depth of the surface layer C becomes larger compared with a case where the width Wd of the dark parts is smaller, and therefore, the amount of information about the surface layer C that can be imaged in the form of a surface layer image increases, whereas the depth of the deep layer D remains constant regardless of the width Wd of the dark parts, and therefore, the amount of information about the deep layer D decreases. In order to ensure a good balance between the amount of information about the surface layer C in the surface layer image and the amount of information about the deep layer D in the deep layer image, it is preferable that the width Wd of the dark parts on the surface B of the biological tissue A be in a range from 0.005 mm to 25 mm.

When the width Wd of the dark parts is less than 0.005 mm, the proportion of the internally scattered light Ld that is internally scattered around from the projection regions of the bright parts to the projection regions of the dark parts increases, and as a result, the differences between the intensity values Imax and the intensity values Imin become smaller, and the information about the surface layer C included in surface-layer component image and the surface layer image may become insufficient. On the other hand, when the width Wd of the dark parts is greater than 25 mm, the internally scattered light Ld cannot reach the centers of the projection regions of the dark parts, and as a result, the intensity values Imin approach zero, and the information about the deep layer D included in the deep-layer component image and the deep layer image may become insufficient.

In this embodiment, the separated-image creating unit 72 may multiply the surface-layer component image by a coefficient P when creating the surface layer image, as illustrated in the following formula (a'). The separated-image creating unit 72 may multiply the deep-layer component image by a coefficient Q when creating the deep layer image, as illustrated in the following formula (b').

Surface layer image=second illumination image×$P$× surface-layer component image/(surface-layer component image+deep-layer component image) (a')

Deep layer image=second illumination image×$Q$× deep-layer component image(surface-layer component image+deep-layer component image) (b')

With this configuration, it is possible to create a surface layer image in which information about a surface layer is more greatly emphasized in accordance with the coefficient P and it is possible to create a deep layer image in which information about a deep layer is more greatly emphasized in accordance with the coefficient Q.

The separated-image creating unit 72 may create a composite image by combining the surface layer image and the deep layer image. In this case, by setting one of the above coefficients P and Q to be large, it is possible to create a composite image in which one of the information about the surface layer C and the information about the deep layer D is emphasized while retaining both the information about the surface layer C and the information about the deep layer D. Specifically, a composite image in which information about the surface layer C is emphasized can be obtained by increasing the coefficient P and a composite image in which information about the deep layer D is emphasized can be obtained by increasing the coefficient Q. Similarly, by setting one of the above coefficients P and Q to be small, it is possible to create a composite image in which one of the information about the surface layer C and the information about the deep layer D is suppressed while retaining both the information about the surface layer C and the information about the deep layer D.

The coefficients P and Q are set by the user via an input means, which is not illustrated, connected to the body part 3.

It may be possible to set the coefficients P and Q for each pixel. The intensity value Iij of each pixel ij of the composite image can be calculated using the following formula, in which ij (i=1, 2, ..., n, j=1, 2, ..., m) are the positional coordinates of pixels in an n pixel×m pixel image. In the following formula, Pij is a combining ratio of a pixel ij of the surface layer image, and Qij is a combining ratio of a pixel ij of the deep layer image.

$$Iij=Pij*Isij/(Isij+Idij)+Qij*Idij/(Isij+Idij)$$

For example, the user may be able to set the combining ratios Pij and Qij while observing the surface layer image and the deep layer image displayed on a display device.

It may be possible to set the coefficients P and Q for each pixel. An intensity value Ik for a wavelength $\lambda k$ ($k=1, 2, \ldots, 1$) in a composite image can be calculated using the following formula. Isk is an intensity value for a surface layer image at a wavelength $\lambda k$, Idk is an intensity value for a deep layer image at the wavelength λk, Pk is a combining ratio for the surface layer image at the wavelength λk, and Qk is a combining ratio for the deep layer image at the wavelength λk.

$$Ik=Pk*Isk/(Isk+Idk)+Qk*Idk/(Isk+Idk)$$

For example, the user may be able to set the composition ratios Pk and Qk while observing the surface layer image and the deep layer image displayed on a display device.

In this embodiment, the intensity-distribution changing unit 5 may change the intensity distribution of the illumination light L1 in a discontinuous manner between two bright-dark patterns in which the bright parts and the dark parts are reversed, as illustrated in FIGS. 3A to 3F, or alternatively, may continuously change the intensity distribution of the illumination light L1 between two bright-dark patterns.

In the case where the bright-dark patterns are continuously changed in this manner, the imaging unit 6 may image three or more first illumination images in which the positions of the projection regions of the bright parts and the projection regions of the dark parts are different from each other by performing image capturing at three or more time points at which the positions of the bright parts and the dark parts are different from each other. The separation processing unit 71 and the separated-image creating unit 72 may create a surface-layer component image and a deep-layer component image from three or more first illumination images. In this case, since three or more intensity values are obtained for each pixel at each position, it is sufficient to calculate the maximum intensity value as Imax and the minimum intensity value as Imin.

Figure 10:
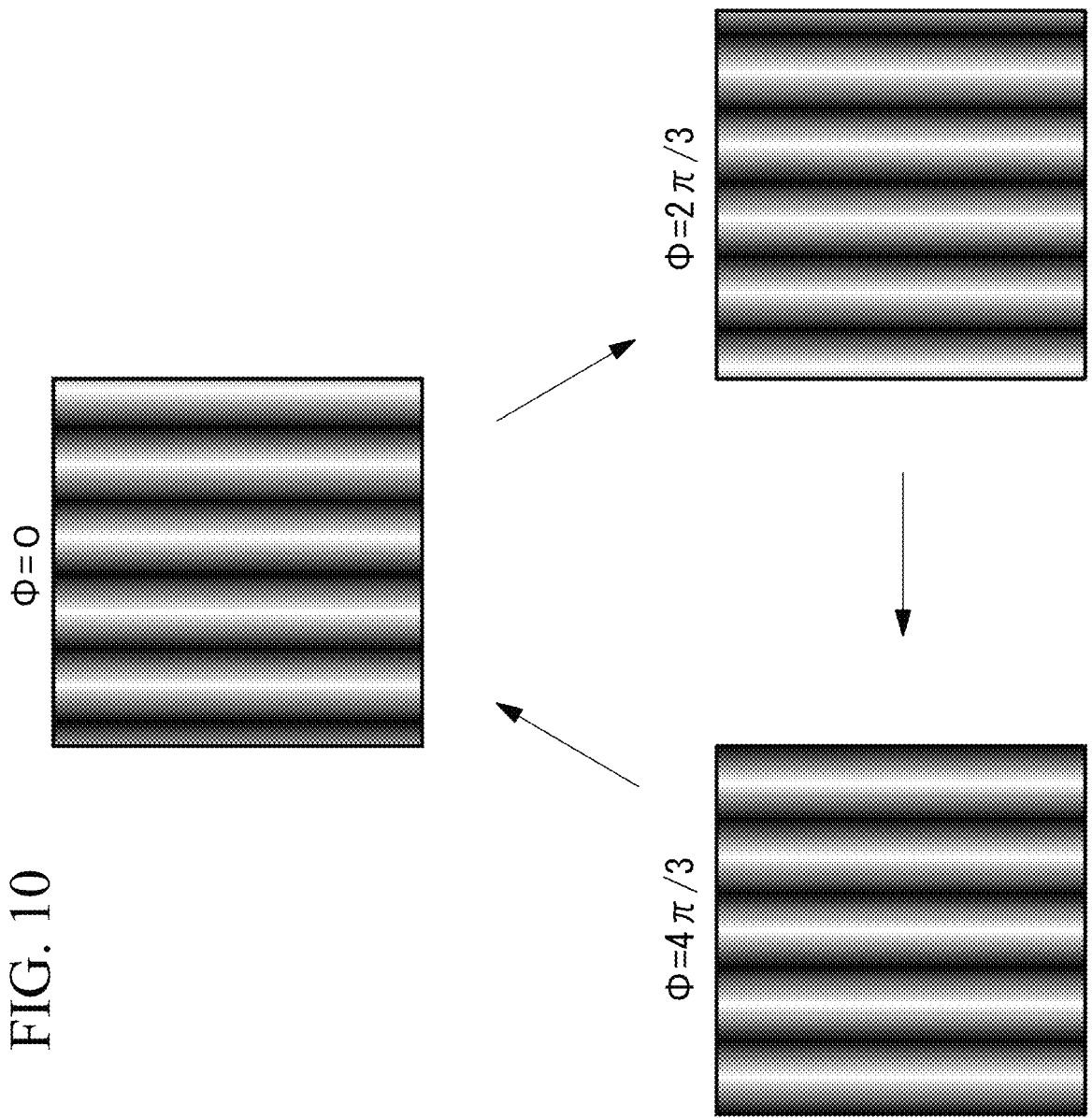
FIG. 10 is a diagram for explaining a method for calculating intensity values Imax and Imin using a phase shift method.

In this embodiment, the intensity values in two first illumination images are used as the intensity values Imax and Imin, but in the case where the bright-dark pattern is a linear stripe pattern in which the intensity changes sinusoidally as illustrated in FIGS. 3B and 4B, the intensity values Imax and Imin of each pixel may be calculated using a phase shift method. With the phase shift method, as illustrated in FIG. 10, the maximum intensity value Imax and the minimum intensity value Imin of each pixel can be obtained from three first illumination images in which the phases Φ of the bright-dark patterns are different from each other. Therefore, it is possible to create a surface layer image and a deep layer image having a resolution identical to that of the second illumination image by using a small number of first illumination images.

In this embodiment, the first illumination light L1 having a structured bright-dark pattern is generated by the liquid crystal element 41b provided inside the body part 3, but the configuration of the first illumination unit 41 is not limited to this example and the first illumination light L1 may be generated using another method.

Figure 11A:
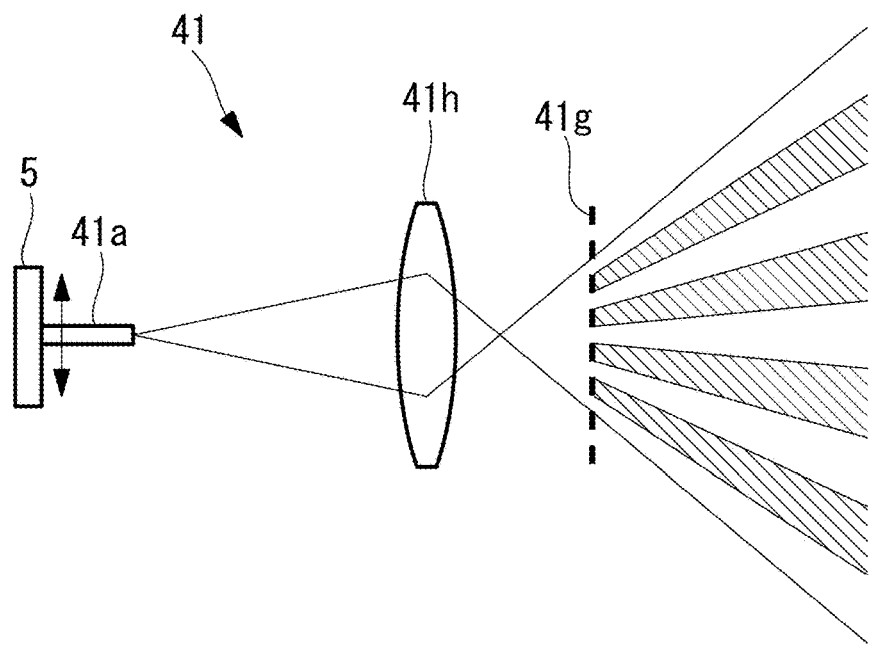
FIG. 11A is a diagram illustrating another example configuration of a first illumination unit and an intensity-distribution changing unit.
Figure 11B:
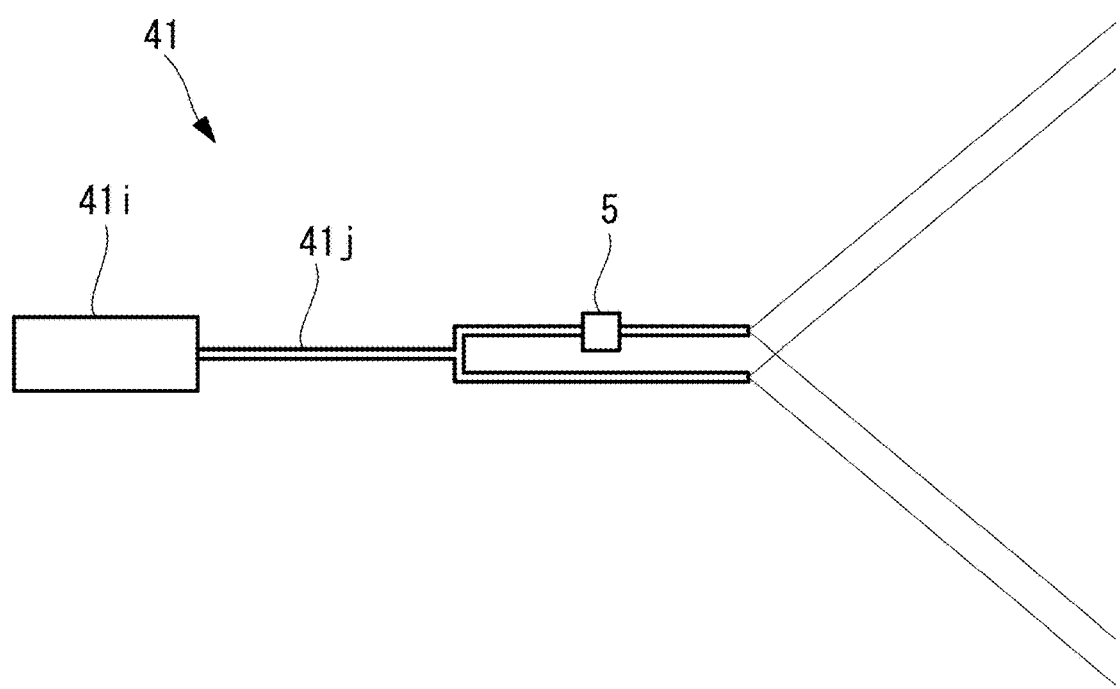
FIG. 11B is a diagram illustrating another example configuration of the first illumination unit and the intensity-distribution changing unit.
Figure 11C:
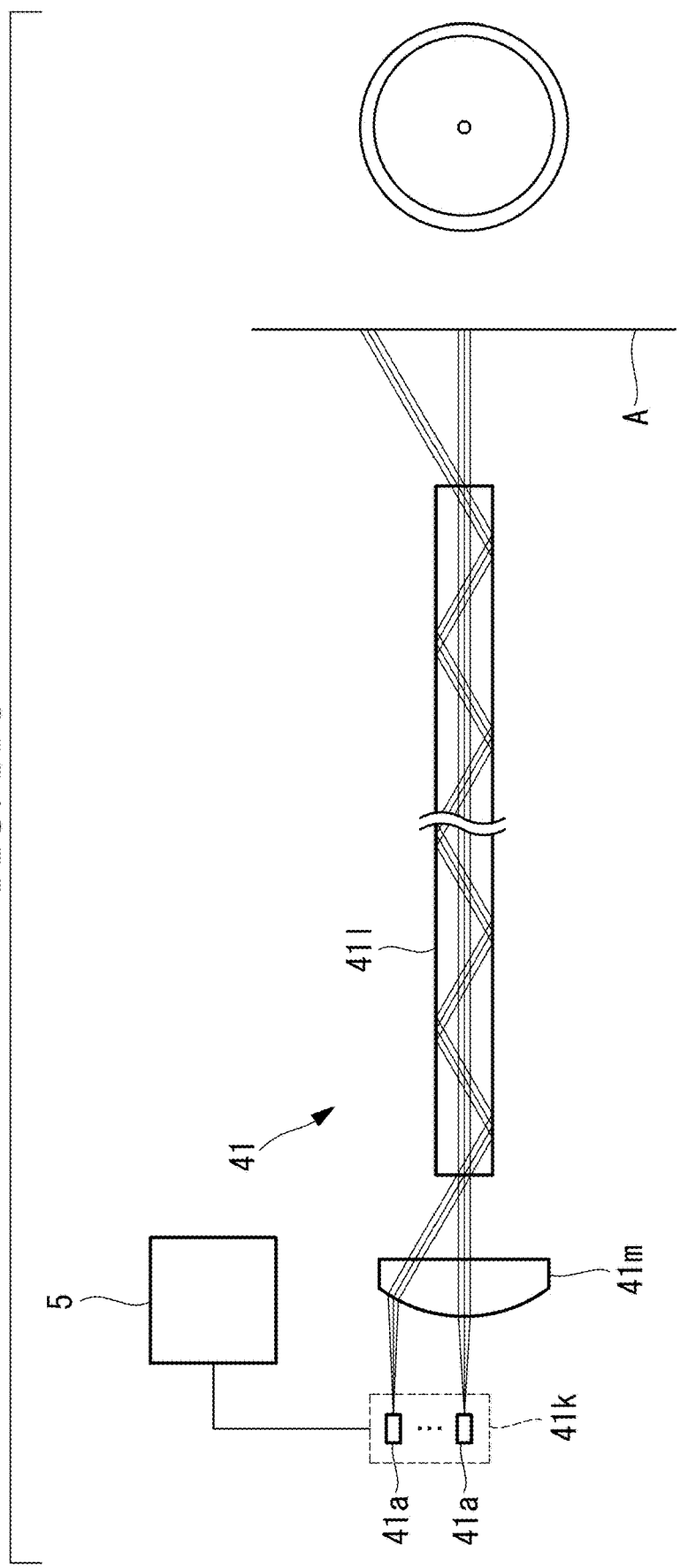
FIG. 11C is a diagram illustrating another example configuration of the first illumination unit and the intensity-distribution changing unit.

FIGS. 11A to 11C illustrate modifications of the configurations of the first illumination unit 41 and the intensity-distribution changing unit 5.

The first illumination unit 41 in FIG. 11A forms a bright-dark pattern on the surface B of the biological tissue A in the manner of a shadow and includes the light source 41a and a mask 41g provided at a distal end of the endoscope 2.

The mask 41g is, for example, a light-blocking substrate having openings that serve as light-transmitting regions or a transparent substrate having light-blocking films that serve as light-blocking regions. White light output from the light source 41a is transmitted through the mask 41g and as a result the first illumination light L1 having a bright-dark pattern is generated, and a projection pattern of the mask 41g is projected onto the biological tissue A. A lens 41h that changes the divergence angle of the white light so that the illumination light L1 radiated onto the biological tissue A comes to have a desired divergence angle may be provided between the light source 41a and the mask 41g.

The intensity distribution of the white light can be changed over time by making the intensity-distribution changing unit 5 function as an actuator that moves at least one of the light source 41a and the mask 41g and by moving the light source 41a and the mask 41g relative to each other in a direction that intersects the optical axis of the white light.

Rather than moving a single light source 41a, the intensity-distribution changing unit 5 may instead be made to function as a control element that controls turning on and turning off of a plurality of light sources 41a so that some of the plurality of light sources 41a are turned on. In other words, a plurality of light sources 41a may be arranged in a direction substantially parallel to the mask 41g and the intensity-distribution changing unit 5 can change the intensity distribution over time by changing which light sources 41a are turned on.

The first illumination unit 41 in FIG. 11B uses light interference fringes as a bright-dark pattern and includes a laser light source 41i and an optical path 41j that splits light output from the laser light source 41i into two light beams and emits the two light beams. The optical path 41j is formed of an optical fiber, for example. Interference fringes having a sinusoidal intensity profile are generated as a bright-dark pattern when the two light beams emitted from the optical path 41j interfere with each other. The intensity-distribution changing unit 5 is an optical element that is provided on one optical path out of the optical paths of the two split light beams and changes the optical path length. The intensity-distribution changing unit 5 shifts the positions of the interference fringes in a direction perpendicular to the optical axis of the illumination light by changing the optical path length of one of the two light beams.

The first illumination unit 41 in FIG. 11C includes a light source array 41k and a light guide member 41l that guides the light while preserving the incidence angle of the light with respect to the optical axis. The light source array 41k includes a plurality of light sources 41a that are arranged so that the light incidence angles thereof with respect to the incident end of the light guide member 41l are different from each other. In FIG. 11C, the plurality of light sources 41a are arranged in one row, but the plurality of light sources 41a may instead be two-dimensionally arranged. The light guide member 41l is a rod lens or a multi-mode fiber, for example.

The white light emitted from the light sources 41a is converted into parallel light beams by a lens 41m and is incident on the incident end of the light guide member 41l. The light that has entered the light guide member 41l is guided through the inside of the light guide member 41l while preserving the angle thereof, and the light is emitted toward the biological tissue A from the emission end of the light guide member 41l at the same angle as the light had at the incident end. The light undergoes repeated reflection inside the light guide member 41l and spreads in the circumferential direction, and consequently the light emitted from the light guide member 41l has an annular shape. Therefore, first illumination light L1 having a concentric circle pattern, as illustrated in FIG. 3, is generated by simultaneously turning on the plurality of light sources 41a.

The intensity-distribution changing unit 5 is a control element that controls turning on and turning off of the light sources 41a, and the intensity-distribution changing unit 5 changes the intensity distribution by controlling turning on and turning off of each light source 41a and changing which light sources 41a are turned on.

Rather than changing which light sources 41a are turned on, the intensity-distribution changing unit 5 may instead be made to function as an actuator that moves the light sources 41a in a direction that intersects the optical axis.

In this embodiment, the first illumination unit 41 is preferably configured so as to emit first illumination light L1 consisting of a diverging light beam toward the biological tissue A so that the bright-dark pattern projected onto the surface B of the biological tissue A is enlarged in proportion to the imaging distance between the biological tissue A and the imaging unit 6.

The boundary between the depth of the information contained in the surface-layer component image and the depth of the information contained in the deep-layer component image depends on the period between the bright parts and dark parts. As the period between the bright parts and the dark parts increases, the amount of information contained in the surface-layer component image increases. Therefore, a surface-layer component image and a deep-layer component image that contain information at different depths can be imaged by changing the imaging distance and enlarging or shrinking the bright-dark pattern on the surface B of the biological tissue A.

The period between the bright parts and the dark parts on the surface B of the biological tissue A may be changed by enlarging or shrinking the entire bright-dark pattern by changing the imaging distance, but alternatively the spatial period between the bright parts and the dark parts in the bright-dark pattern of the first illumination light L1 may be changed.

For example, the period between the bright parts and the dark parts may be changed via electrical control performed by the liquid crystal element 41b of the first illumination unit 41.

Three or more separated images may be created using two or more first illumination images imaged by radiating first illumination light L1 having different spatial periods between the bright parts and the dark parts, i.e., different dark part widths. That is, the separation processing unit 71 may separate three or more component images containing information at different depths from two or more first illumination images and the separated-image creating unit 72 may create three or more separated images containing information at different depths by using the three or more component images.

In the case where a bright-dark pattern is formed via projection as illustrated in FIG. 11A, the period between the bright parts and the dark parts may be changed by changing the distance between the light source 41a and the mask 41g by moving the light source 41a and the mask 41g relative to each other in the optical axis direction of the white light.

Alternatively, a zoom lens consisting of a plurality of lenses and in which at least one lens is movable in the optical axis direction may be provided on the optical path of the first illumination light L1.

Figure 2B:
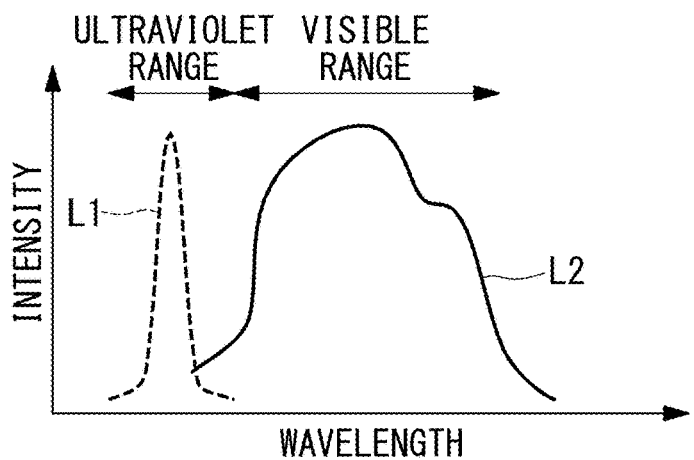
FIG. 2B is a diagram illustrating a modification of the wavelength bands of the first illumination light and the second illumination light.
Figure 2C:
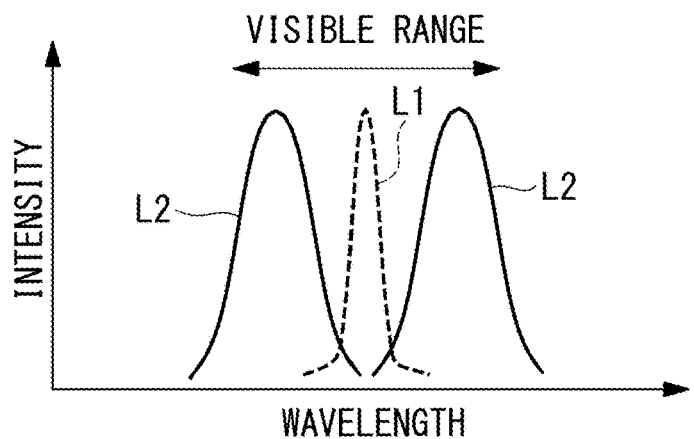
FIG. 2C is a diagram illustrating another modification of the wavelength bands of the first illumination light and the second illumination light.
Figure 2D:
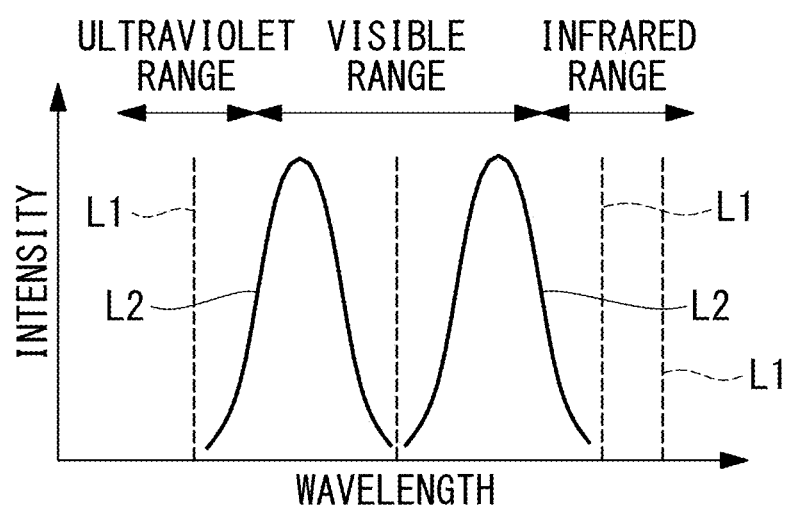
FIG. 2D is a diagram illustrating another modification of the wavelength bands of the first illumination light and the second illumination light.

In this embodiment, infrared light is used as the first illumination light L1, but alternatively light having another wavelength band may be used. FIGS. 2B to 2D illustrate modifications of the wavelength band of the first illumination light L1.

As illustrated in FIG. 2B, the first illumination light L1 may be ultraviolet light.

As illustrated in FIGS. 2C and 2D, in the case where the second illumination light L2 is composed of a plurality of light beams and the wavelength band in which the second illumination light L2 has almost no intensity is in the visible range, first illumination light L1 having a wavelength band in the visible range may be used. The first illumination light L1 may be light having a certain spectral width, as illustrated in FIG. 2C or may be light having a single wavelength, as illustrated in FIG. 2D. As illustrated in FIG. 2D, the first illumination light L1 may include a plurality of light beams having different wavelength bands.

The second illumination light L2 is not limited to wide-band light having a spectrum over substantially the entire visible range, such as white light, and may instead be light having a spectrum only in a specific wavelength range. For example, the spectra of the first illumination light L1 and the second illumination light L2 in FIGS. 2A to 2D may be reversed. In other words, the first illumination light L1 may be wide-band light such as white light and the second illumination light L2 may be narrow-band light or single-wavelength light.

Figure 12:
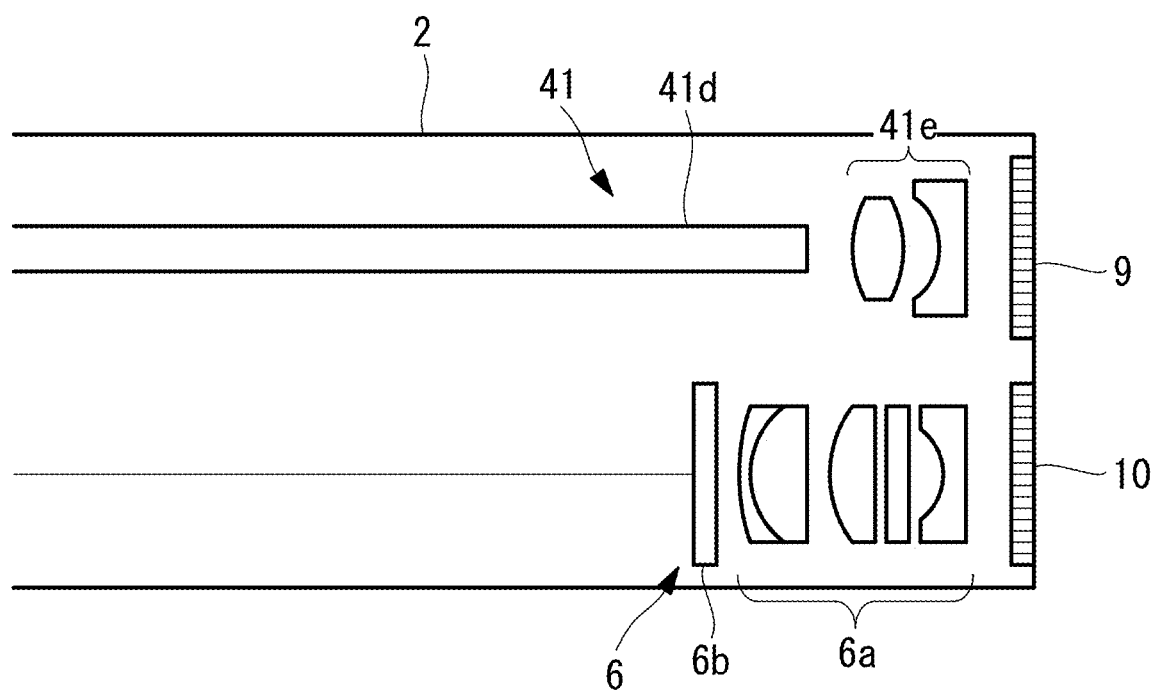
FIG. 12 is a partial configuration diagram of a modification of an endoscope system including a polarizer.

In this embodiment, information about the biological tissue A is separated into two sets of information, namely, information about the surface B and the surface layer C and information about the deep layer D, but the information may instead be further separated into information about the surface B and information about the surface layer C by using polarization as illustrated in FIG. 12. In FIG. 12, illustration of the second illumination unit 42 is omitted.

A polarizer 9 that controls the polarization state of the first illumination light L1 emitted from the first illumination unit 41 and a polarizer 10 that selects the polarization state of light incident on the imaging unit 6 from the biological tissue A are provided at the distal end of the endoscope 2. A first illumination image that includes the surface scattered light Ls and the specular light Lr can be imaged by making the polarization direction of the polarizer 10 match the polarization direction of the polarizer 9, and a first illumination image that includes the surface scattered light Ls but does not include the specular light Lr can be imaged by making the polarization direction of the polarizer 10 perpendicular to the polarization direction of the polarizer 9.

As a result, the following aspect is read from the above described embodiment of the present invention.

One aspect of the present invention provides an endoscope system that includes: a first illumination unit that emits, toward a subject, first illumination light that is for imaging two sets of image information about the subject at different depths; a second illumination unit that emits second illumination light toward the subject; an imaging unit that images a first illumination image of the subject illuminated with the first illumination light and a second illumination image of the subject illuminated with the second illumination light; a separation processing unit that separates the two sets of image information from the first illumination image; and a separated-image creating unit that processes the second illumination image using the two sets of image information to create two separated images respectively containing a lot of information about the subject at the different depths. The first illumination light is light of a different wavelength band from the second illumination light. The first illumination unit and the second illumination unit simultaneously emit the first illumination light and the second illumination light. The imaging unit captures images of the subject illuminated with the first illumination light and the second illumination light to simultaneously image the first illumination image and the second illumination image.

According to this aspect, a second illumination image is imaged by the imaging unit capturing an image of the subject illuminated with the second illumination light. On the other hand, the first illumination image is imaged by the imaging unit capturing an image of the subject illuminated with the first illumination light and two sets of image information that are contained in the first illumination image and are located at different depths are separated from the first illumination image by the separation processing unit. Two separated images that contain information about the subject at different depths can be created by processing the second illumination image using the two sets of image information.

In this case, since the wavelength band of the first illumination light and the wavelength band of the second illumination light are different from each other, the imaging unit can separate and image the first illumination image and the second illumination image on the basis of wavelength. Therefore, separated images can be created without a reduction in frame rate by simultaneously imaging the first illumination image and the second illumination image by performing image capturing one time on the subject illuminated with both the first illumination light and the second illumination light.

In the above aspect, the first illumination light may be infrared light.

With this configuration, white light having wavelengths across the entire visible range can be used as the second illumination light. In addition, the longer the wavelength of the first illumination light is, the deeper the position that the first illumination light can reach inside the subject, and therefore a separated image containing information at a deeper position can be created by using infrared light as the first illumination light.

In the above aspect, the first illumination light may have a spatially non-uniform intensity distribution including bright parts and dark parts in a light beam cross section perpendicular to an optical axis.

When the subject, which is a scattering body, is irradiated with the illumination light, specularly reflected (specular) light that is specularly reflected at a surface of the subject, surface scattered light that is emitted from the surface of the subject after having undergone scattering in a surface layer inside the subject, and internally scattered light that is emitted from the surface of the subject after having undergone scattering in a deep layer inside the subject are generated. The internally scattered light is spatially separated from the specular light and the surface scattered light as a result of the subject being irradiated with the first illumination light having a spatially non-uniform intensity distribution. In other words, although the specular light, the surface scattered light, and the internally scattered light are generated in the bright parts, generation of the internally scattered light which is internally scattered around from the bright parts to the dark parts is dominant in the dark parts. Therefore, image information about a deep layer can be separated from regions of the first illumination image corresponding to dark parts and image information about the surface and a surface layer can be separated from regions of the first illumination image corresponding to the bright parts.

In the above aspect, the bright parts and the dark parts included in the first illumination light may have a band-like shape, and the bright parts and the dark parts may form a striped pattern in which the bright parts and the dark parts alternate in a repeating manner in a width direction.

With this configuration, internally scattered light can be effectively separated by using a simple bright-dark pattern.

In addition, since the positions of the bright parts and the dark parts of the striped intensity distribution can be swapped by simply moving the bright parts and dark parts of the striped intensity distribution in only the width direction, the intensity distribution of the illumination light can be easily changed over time.

In the above aspect, the bright parts and the dark parts included in the first illumination light may have a sinusoidal intensity profile in the width direction.

Thus, the subject is irradiated with the first illumination light in which the intensity spatially changes in a sinusoidal manner and the intensity values for the separated image of the surface layer when the light having the highest intensity is applied and the intensity values for the separated image of the deep layer when the light having the highest intensity is not applied can be calculated using a phase shift method, and excellent separated images having high resolution can be created from a small number of first illumination images.

In the above aspect, a wavelength spectral shape of the first illumination light may be a single wavelength.

In the above aspect, the separation processing unit may separate three or more sets of image information from two or more first illumination images imaged by radiating first illumination light beams having dark parts of different widths, and the separated-image creating unit may create three or more separated images using the three or more sets of image information.

Thus, it is possible to create three or more separated images containing a lot of information at different depths by using a plurality of first illumination images of the subject illuminated with first illumination light beams having dark parts of different widths.

REFERENCE SIGNS LIST 1 endoscope system
2 endoscope
3 body part
41 first illumination unit
42 second illumination unit
5 intensity-distribution changing unit
6 imaging unit
7 image processing unit
71 separation processing unit
72 separated-image creating unit
L1 first illumination light
L2 second illumination light
A biological tissue
B surface
C surface layer
D deep layer

The invention claimed is:

1. An endoscope system comprising:
a first light source configured to emit, toward a subject, first illumination light that is for imaging two sets of image information about the subject at different depths;
a second light source configured to emit second illumination light toward the subject; and
a processor comprising hardware, the processor being configured to:
receive a first illumination image of the subject illuminated with the first illumination light and a second illumination image of the subject illuminated with the second illumination light;
separate the two sets of image information from the first illumination image; and process the second illumination image using the two sets of image information to create two separated images respectively containing information about the subject at the different depths;

wherein the first illumination light has a spatially non-uniform intensity distribution including bright portions and dark portion in a light beam cross section perpendicular to an optical axis, the first illumination light is light of a different wavelength band from the second illumination light, the first light source and the second light source simultaneously emit the first illumination light and the second illumination light, the first illumination image of the subject illuminated with the first illumination light and the second illumination image of the subject illuminated with the second illumination light are simultaneously received, a first set of the two sets of image information is a deep layer component image that contains more information about a deep layer of the subject than a second set of the two sets, and the second set of the two sets of image information is a surface-layer component image that contains more information about a surface and a surface layer of the subject than the deep layer component image, and the processor is configured to:
- create a deep layer image in which information about the deep layer of the subject is emphasized over information about the surface and the surface layer of the subject by using and processing the deep layer component image and the surface layer component image, and
- create a surface layer image in which the information about the surface and the surface layer of the subject is emphasized over the deep layer image by using and processing the surface layer component image and the deep layer component image.

2. The endoscope system according to claim 1, wherein the first illumination light is infrared light.

3. The endoscope system according to claim 1, wherein the bright portions and the dark portions included in the first illumination light have a band-like shape, and the bright portions and the dark portions form a striped pattern in which the bright portions and the dark portions alternate in a repeating manner in a width direction.

4. The endoscope system according to claim 3, wherein the bright portions and the dark portions included in the first illumination light have a sinusoidal intensity profile in the width direction.

5. The endoscope system according to claim 1, wherein a wavelength spectral shape of the first illumination light is a single wavelength.

6. The endoscope system according to claim 1, wherein the processor:
- separates three or more sets of image information from two or more first illumination images imaged by radiating first illumination light beams having dark portions of different widths, and
- creates three or more separated images using the three or more sets of image information.

7. The endoscope system according to claim 1, wherein the processor creates the surface layer image on the basis of formula (a) below and creates the deep layer image on the basis of formula (b) below:

$$\text{surface layer image} = \text{second illumination image} \times \text{surface-layer component image}/(\text{surface-layer component image} + \text{deep-layer component image}) \quad (a)$$

$$\text{deep layer image} = \text{second illumination image} \times \text{deep-layer component image} (\text{surface-layer component image} + \text{deep-layer component image}) \quad (b).$$

8. The endoscope system according to claim 1, wherein the processor creates the surface layer image on the basis of formula (a) below and creates the deep layer image on the basis of formula (b) below:

$$\text{surface layer image} = \text{second illumination image} \times P \times \text{surface-layer component image}/(\text{surface-layer component image} + \text{deep-layer component image}) \quad (a)$$

$$\text{deep layer image} = \text{second illumination image} \times Q \times \text{deep-layer component image}/(\text{surface-layer component image} + \text{deep-layer component image}) \quad (b)$$

where, $P$ and $Q$ are coefficients.

* * * * *